US007674226B2

(12) United States Patent
Nadeau

(10) Patent No.: US 7,674,226 B2
(45) Date of Patent: Mar. 9, 2010

(54) METHOD FOR ENHANCED PERFORMANCE TRAINING

(76) Inventor: Gary Nadeau, 659 Vedette St., Reynoldsburg, OH (US) 43068

(*) Notice: Subject to any disclaimer, the term of this patent is extended or adjusted under 35 U.S.C. 154(b) by 743 days.

(21) Appl. No.: 11/342,108

(22) Filed: Jan. 27, 2006

(65) Prior Publication Data
US 2007/0179350 A1 Aug. 2, 2007

(51) Int. Cl.
A61B 5/00 (2006.01)
A61B 5/08 (2006.01)
A61B 5/02 (2006.01)
(52) U.S. Cl. .................. 600/300; 600/529; 600/483
(58) Field of Classification Search ................ 600/300, 600/529–543
See application file for complete search history.

(56) References Cited

U.S. PATENT DOCUMENTS

| 6,176,241 | B1 * | 1/2001 | Blau et al. | 128/898 |
| 6,411,841 | B2 | 6/2002 | Heikkila | |
| 6,554,776 | B1 * | 4/2003 | Snow et al. | 600/532 |
| 7,108,659 | B2 * | 9/2006 | Ross et al. | 600/529 |
| 2004/0186390 | A1 | 9/2004 | Ross et al. | |

OTHER PUBLICATIONS

Tingay et al. "Monitoring of end tidal carbon dioxide and transcutaneous carbon dioxide during neonatal transport" Arch. Dis. Child. Feta Neonatal Ed. 2004;90;F523-526. Apr. 29, 2005.*
Griffin et al. "Comparison of end-tidal and transcutaneous measures of carbon dioxide during general anaesthesia in severely obese adults" British Journal of Anaesthesia 91 (4): 498-501 (2003).*
Casati et al. "Transcutaneous monitoring of partial pressure of carbon dioxide in the elderly patient: a prospective, clinical comparison with end-tidal monitoring" Journal of Clinical Anesthesia (2006) 18, 436-440.*
Michael G. Levitzky, Pulmonary Physiology—Lange Physiology Series, 2003, pp. 163-183, McGraw Hill.
Kenneth Axen, Kethleen Vermitsky Axen, Illustrated Principles of Exercise Physiology, 2001,pp. 145-186, Prentice Hall, Upper Saddle River, NJ USA.

(Continued)

Primary Examiner—Charles A Marmor, II
Assistant Examiner—Christian Y Jang
(74) Attorney, Agent, or Firm—Gallagher & Dawsey Co.,LPA; Michael J. Gallagher; David J. Dawsey

(57) ABSTRACT

A method for enhanced exercise training or performance utilizing intentional controlled tachypnea and somatic sensory alkalosis biofeedback training to maintain an essentially non-acidic state during exercise. A trainee is instructed to decrease measured transcutaneous $CO_2$ levels by increased ventilation and to correlate measured transcutaneous $CO_2$ levels with subjective somatic symptoms. Studies under exercise conditions measure the intensity of exercise correlating to an onset in blood acid accumulation in the trainee and such level of intensity is in turn correlated with a predetermined heart rate. The trainee is then instructed to use heart rate and somatic sensory changes as a guide to the need for increased ventilation to lower blood $CO_2$. In another embodiment, the method of the instant invention utilizes intentional controlled tachypnea to increase maximum breath holding time.

24 Claims, 18 Drawing Sheets

OTHER PUBLICATIONS

Terence G. Favero, Sacroplasmic Reticulum Ca2+ Release and Muscle Fatigue, J. Appl. Physiol., Aug. 1999, pp. 471-483, vol. 86 Issue 2.

R. H. Fitts, Cellular Mechanisms of Muscle Fatigue, Physiol. Rev., Jan. 1994, pp. 49-94, vol. 71 Issue 1, USA.

Michael J. Mckenna and Others, Sprint Training Enhances Ionic Regulation During Intense Exercise in Men, J. Physiol., 1997, pp. 687-702, vol. 501.3.

Jens Jung Nielsen and Others, Effects of High-Intesity Intermittent Training on Ka Kinetics and Perf. in Human Skeletal Muscle, J. Physiol., 2003, pp. 857-870, vol. 554.3.

Carsten Juel and Others, Effect of High-Int. Interm. Training on Lactate and H+ Release From Hmn Skeletal Muscle, Am. J. Physiol.—Endocrin Metab, 2004, E245-E251, vol. 286.

Bruno Grassi and Others, Blood Lactate Accum. and Muscle Deoxygenation During Incremental Exercise, J. Appl. Physiol., Jul. 1999, pp. 348-355, vol. 87 Issue 1.

Mio Tonouchi and Others, Mscl Contraction Incrs Lactate Transport While Reducing Sarcolemmal MCT4, but not MCT1, Am. J. Physiol.—Endocrin. Metab., 2002, E1062-E1069, V282I5.

Shona L. Halson and Others, Time Crs of Performance Chngs and Fatigue Markers During Intesified Training in Trained Cyclist, J. Appl. Physiol., 2002, pp. 947-956, vol. 93 Iss 3.

Graydon H. Raymer and Others, Metabolic Effects of Induced Alkalosis During Progressive Forearm Exercise to Fatigue, J. Appl. Physiol., 2004, pp. 2050-2056, vol. 96.

R. J. Connett and Others, Lactate Efflux is Unrelated to Intracellular PO2 in Working Red Muscle in Situ, J. Appl. Physiol. , 1986, pp. 402-408, vol. 61 Issue 2.

M.G. Hollidge-Horvat and Others, Effct of Indcd Metabolic Acidosis on Hmn Skeletal Mscl Metabolism During Exerc., Am. J. Physiol. Endocrinal Metab, E647-E658, 1999, vol. 277 I4.

Marcie G. Berger and Others, Intracell. Acidosis Diff. Reg. Kv Chnnls in Coronary and Pulmonary Vascular Mscl, Am. J. Physiol. Heart Circ. Physiol, H1351-H1359,1998, vol. 275 I4.

R. Jorge Zeballos and Others, Comp. of Pulmonary Gas Exchg Meas. Between Increm. and Constant Work Exercise Above the Anaerobic Threshold, Human Pert. Lab. Dept. of Clinic.Inv.

Johnson BD and Others, Mech Constraints on Exercise Hyperpnea in Endurance Athletes, John Rankin Lab. of Pulmonary Med. Univ of Wis, pp. 874-886, 1992, vol. 73 Issue 3.

Jonville S. and Others, Contribution of Respiratory Acidosis to Diaphragmatic Fatigue at Exercise, J. Appl. Physiol., pp. 1256-1269, Oct. 1997, vol. 83 Issue 4.

Yanos J. and Others, The effect of Respiratory and Latic Acidosis on Diaphragm Function, Int J Sports Med., pp. 154-159, 1981, vol. 2 Issue 3, abs.

Inbar O and Others, Relationships Between Leg Muscle Fiber Type Distrubution and Leg Exercise Performance, Int J Sports Med., pp. 284-293, 2004, vol. 24 Issue 4, abs.

McConnel AK and Romer LM, Respiratory Muscle in Healthy Humans: Resolving the Controversy, Int J Sports Med., pp. 48-52, 1989, vol. 10 Issue 1, abs.

Dodd SL and Others, Exercise Perf. Following Intense Short-Term Ventillatory Work, Int J Sports Med, 2001, pp. 803-809, vol. 33 Issue 5, abs.

Volianitis S and Others, Inspiratory Muscle Training Impr. Rowing Perf., Chest, 1991, pp. 136-142, vol. 100 Issue 1, abs.

Blackie SP and Others, Normal Values and Ranges for Ventilation and Breathing Pattern at Maximal Exercise, Univ. of British Columb.—Pulmonary Research Laboratory, abs.

Jonathan Myers and Eun Ashley, Dangerous Curves—A Perspective on Exercise, Lactate, and the Anaerobic Threshold, Chest, 1997, pp. 787-795, vol. 111.

S. Ratel and Others, Acid Balance During Repeated Cycling Sprints in Boys and Men, J. Appl. Physiol, 2002, pp. 479-485, vol. 92 Issue 2.

Forster HV and Pan LG, Breathing During Exercise: Demands, Regulation, Limitation, Adv Exp Med Biol, 1998, pp. 257-276, vol. 227, abs.

Neilsen HB and Others, Bicarbonate Attenuates Aterial Desaturation During Maximal Exerc in Humans, The Copenhagan Muscle Research Center, Dept Anesthesia, Copenhagen Denmark, abs.

Craig A. Harms and Others, Effects of Respiratory Muscle Work on Exercise Performance, J Appl Physiol, 2000, pp. 131-138, vol. 89.

Koskolou and Mckenzie, Aterial Hypoxia and Performance During Intense Exercise, Dept. Sports Sci, Allan McGavin Sports Med. Centre, Univ British Columb, Vancouver Canada, abs.

Lee C Coudain L and Others, Metab Conseq of Reduced Freq Breathing During Submaximal Exerc at Mod Altitude, Eur J Appl Physiol Occup Physiol, 1990, pp. 289-293, vol. 61I 3-4, abs.

Wexels JC and Others, Effects of Hypo- and Hyper-Capnia on Myocardial Blood Flow and Metab. During Epineph. Infus. in the Dog, Can. J. Physiol. Pharmacol., 1986, pp. 44-49, V64, abs.

Jastrzembski-Wieber S and Others, Learning Occurs with Repetitions of Inspiratory Loading, Chest, 2003, pp. 432S-433S, vol. 123(3 Suppl), abs.

Harms CA and Dempsy JA, Cardiovascular Consequences of Exercise Hyperpnea, Dept. of Kinesiology, Kans. State Univ., Manhattan Kans, USA, abs.

R.S. Richardson and Others, Evid. of Skel Mscl Metab. Rsrv During Whle Body Exerc. in Patients with Chronic Obstr. Pulmon. Disease, Am. J. Respir. Crit. Care Med, V159 3,1999.

Mahler DA and Others, Ventilatory Responses at Rest and During Exercise in Marathon Runners, abs.

Hopkins SR and Others, Pulmonary Gas Exchanfe during Exercise in Women: Effects of Exercise Type and Work Increment, Div. of Physiol. Dept. of Med. Univ of Ca., San Diego, abs.

Dempsey JA and Others, The John Sutton Lecture: CSEP, 2002]. Pulmonary Systems Limitation to Exercise in Health, Can. J. Physiol. Pharmacol., 2003, pp. s2-24, V28 Suppl, abs.

Dempsey JA and Wagner PD, Exercise-Induced Arterial Hypoxemia, Exer Sport Sci Rev, 1999, pp. 37-62, vol. 27, abs.

Prefaut C and Others, Exercise-Induced Arterial Hypoxaemia in Athletes: a review, Sports Med, 2000, pp. 47-61, vol. 30 Issue 1, abs.

Anthony J. Rice and Others, Pulmonary Gas Exchange During Exercise in Highly Trained Cyclists with Arterial Hypoxemia, J Appl Physiol, 1999, pp. 1802-1812, vol. 87.

Rice AJ and Others, Pulmonary Gas Exchange During Exercise in Highly Trained Cyclists with Arterial Hypoxemia, Dept. of Thoracic Med., Royal Adellaide, S. Australia, abs.

Wetter TJ and Others, Effects of Exhaustive Endur. Exercise on Pulmonary Gas Exchg and Airway Funct in Women, Dept. of Prev. Med., John Rankin Lab. of Pulm. Med., Univ Wisc, abs.

Fregosi RF and Dempsey JA, Arterial Bloos Acid-Base Regulation During Exercise in Rats, J Appl Physiol, 1984, pp. 396-402, vol. 57 Issue 2, abs.

Henning B. Nielsen and Others, Barcarbonate Attenuates Arterial Desaturation During Maximal Exercise in Humans, From Site: Genesis—Bethesda, The Copenhagen Muscle Research.

Wilkes D and Others, Effect of Acute Induced Metabolic Alkalosis on 800-m Racing Time, Med Sci Sports Exerc, 1983, pp. 277-280, vol. 15 Issue 4, abs.

Birds SR and Others, The Effect of Sodium Bicarbonate Ingestion on 1500-m Racing Time, J Sports Sci, 1995, pp. 399-403, vol. 13 Issue 5, abs.

Goldfinch J and Others, Induced Metabolic Alkalosis and Its Effects on 400-m Racing Time, Eur J Appl Physiol Occup Physiol, 1998, pp. 45-48, vol. 57 Issue 1, abs.

McNaughton L and Others, Anaerobic Work and Poer Output During Cycle Ergometer Exercise: Effects of Bicarbonate Loading, J Sports Sci, 1991, pp. 151-160, vol. 9 Issue 2, abs.

McNaughton LR, Sodium Bicarbonate Ingestion and its Effects on Anaerobic Exercise of Various Durations, J Sports Sci, 1992, pp. 423-435, vol. 10 Issue 5, abs.

Webster MJ and Others, Effect of Sodium Bicarbonate Ingestion on Exhaustive Resistance Exercise Performance, Med Sci Sports Exerc, 1993, pp. 960-965, vol. 28 Issue 8, abs.

McKenzie DC and Others, Maximal Work Production Following Two Levels of Artificially Induces Metabolic Alkalosis, J Sports Sci, 1986, pp. 35-38, vol. 4 Issue 1, abs.

Portington KJ and Others, Effect of Induced Alkalosis on Exhaustive Leg Press Performance, Med Sci Sports Exerc, 1998, pp. 523-528, vol. 30 Issue 4, abs.

Matson LG and Tran ZV, Effects of Sodium Bicarbonate Ingestion On Anaerobiv Performance: a Meta-Analytical Review, Int J Sport Nutr, 1993 pp. 2-28, vol. 3 Issue 1, abs.

Ibanez J and Others, Blood Lactate and Ammonia in Short-Term Anaerobic Work Followin Induced Alkalosis, J Sports Med Phys Fitness, 1995, pp. 187-193, vol. 35 Issue 3, abs.

Jeyaranjan R and Others, The Effect of Metab Acid-Base Changes on the Ventilatory Changes at the End of Hvy Exerc, Eur J Appl Physiol Occup Physiol, 1989, pp. 405-410, vol. 58, abs.

Hirakoba K and Others, Effect of Acute Sodium Bicarbonate Ingestion on Excess CO2 Output During Incremental Exercise, Eur J Appl Physiol Occup Physiol, pp. 536-541, vol. 66 Is 6, abs.

Gaitanos GC and Others, Repeated Bouts of Sprint Running After Induced Alkalosis, J Sports Sci, 1991, pp. 355-370, vol. 9 Issue 4, abs.

Bouissou P and Others, Metabolic and Bloos Catecholamine Responses to Exercise During Alkalosis, Med Sci Sports Exerc, 1998, pp. 228-232, vol. 20 Issue 3, abs.

Patterson MJ and Others, Effect of Induced Metabolic Alkalosis on Sweat Composition, PMID: 3386500, abs.

Wasserman K, Coupling of External to Cellular Respiration During Exercise: the Wisdom of the Body Revisited, Am J Physiol, 1994, pp. E519-E539, vol. 266 Issue 4 Pt 1, abs.

Stringer W and Others, The VCO2/Vo2 Relationship During Hvy, Const Work Rate Exerc Reflects the Rate of Lactic Acid Accum, Eur J Appl Physiol Occup Physiol, 1995, 25-31, V72, abs.

Wasserman K, Coupling of External to Internal Respiration, Am Rev Respir Dis, 1984, pp. S21-S24, vol. 129 Issue 2 Pt 2, abs.

Dennis SC and Others, Ventilation and Blood Lactate Increases Exponentially During Incremental Exercise, J Sports Sci, 1993, pp. 437-449, vol. 10 Issue 5, abs.

Koike A and Others, Evidence That Diffusion Limitation Determines Oxygen Uptake, J Clin Invest, 1990, pp. 1698-1706 vol. 86 Issue 5, abs.

Zhang YY and Others, The Role of Fitness on VO2 and VCO2 Kinetics in Response to Propor Step Inc in Work Rate, Eur J Applly Phsiol Occup Physiol,1991, 94-100, vol. 63 Issue 2, abs.

Taylor R and Jones NL, The Reduction by Training of CO2 Output During Exercise, Eur J Cardiol, 1979, pp. 53-62, vol. 9 Issue 1, abs.

Yano T, The Differences in CO2 Kinetics During Incremental Exercise Among Sprinters, Middle, and Long Distance Runners, Jpn J Physiol, 1987, pp. 369-378, vol. 37 Issue 3, abs.

Wasserman K and Others, Mechanisms and Patterns of Blood Lactate Increase During Exercise in Man, Med Sci Sports Exerc, 1986, pp. 344-352, vol. 18 Issue 3, abs.

Wasserman K, The Anaerobic Threshold: Definition, Physiological Significance and Identification, Adv Cardiol, 1986, pp. 1-23, vol. 35, abs.

Swain RA and Others, Prolonged Exercise Induces Angiogenesis and Increases Cerebral Blood Volume in Primary Motor Cortex of the Rat, PMID: 12654355, Dept of Pysch, Univ of III, abs.

Jonville S and Others, Contribution of Respiratory Acidosis to Diaphragmatic Fatigue at Exercise, PMID: 12108860, Sports Sci Dept, Univ of Poitiers, France, abs.

Gerrard F Rafferty and Others, Effect of Hypercapnia on Maximal Voluntary Vantilation and Diaphram Fatigue in Normal Humans, Am. J. Respir, 1999, pp. 1567-1571, vol. 160 No. 5.

Spriet LL and Others, Effects of Acidosis on Rat Muscle Metabolism and Performance During Heavy Exercise, Am J Physiol, 1985, pp. C337-C347, vol. 248(3 Pt 1). abs.

Jaun G and Others, Effect of Carbon Dioxide on Diaphragmatic Function in Human Beings, N Engl J Med, 1984, pp. 874-879, vol. 310(14), abs.

Rose CE and Others, Right Ventricular Performance During Increased Afterload Impaired by Hypercapnic Acidosis in Concious Dogs, Circ Res, 1983, pp. 76-84, vol. 52(1), abs.

Johnson BD and Others, Mechnical Constraints in Exercise Hyperpnea in Endurance Athletes, J Appl Physiol, 1992, pp. 874-886, vol. 73(3), abs.

Lucia A and Others, Breathing Pattern in Highly Competitive Cyclist During Incremental Exercise, Eur J Appl Physiol Occup Physiol, PMID: 10344461, 1999, pp. 512-521 vol. 79(6), abs.

Lucia A and Others, Effects of Endurance Training on the Breathing Pattern of Professional Cyclists, Jpn J Physiol, PMID: 11405905, 2001 pp. 133-141, vol. 51(2), abs.

Hoogeveen AR, The Effect of Endurance Training on the Ventilatory Response to Exercise in Elite Cyclist, Eur J Appl Physiol Occup Physiol, 2000, pp. 45-51, vol. 82(1-2), abs.

Lind FG, Respiratory Drive and Breathing Pattern During Exercise in Man, Acta Physiol Scand Suppl, PMID: 6594031, 1984, pp. 1-47, vol. 533, abs.

Alejandro Lucia and Others, The Slow Component of O2 in Professional Cyclist, Dept. de Ciencias Marfologicas y Fisiologia, Univ Europea de Madrid Spain.

Takano N, Respiratory Compensation Pnt During Incremental Exercise as Related to Hypoxic Ventilatory Chemosensitivity and Lactate Inc in Man, Jpn J Physiol,2000,p. 449-455,V50(4), abs.

Artken ML and Others, Influence of Body Size and Gender on Control of Ventilation, Jpn J Physiol, PMID:3087935, 1986, pp. 1894-1899, vol. 60(6), abs.

Scheuermann BW and Kowalchuk JM, Attenuated Respiratory Compensation During Rapidly Incremented Ramp Exercise, Respir Physiol, PMID:9926987,1998, pp. 227-238, vol. 114(3), abs.

Martin BJ and Others, Control of Breathing During Prolonged Exercise, J Appl Physiol, PMID: 6782056, 1981, pp. 27-31, vol. 50(1), abs.

Graydon H. Raymer and Others, Metabolic Effects of Induced Alkalosis During Progressive Forearm Exercise to Fatigue, J Appl Physiol, 2004, pp. 2050-2056, vol. 96.

Smith GL and Others, A Review of the Actions and Control of Intracellular pH in Vasculat Smooth Muscle, Cardiovasc Res, 1998, pp. 316-331, vol. 38(2), abs.

Austin C and Others, Simult Meas of Intracellular pH, Ca and Tension in Rat Mesenteric Vessels: Effects of Extracellular pH, Biochem Biophys Res Commun, 1996, 537-40, V222(2), abs.

Aalkjaer C and Poston L, Effects of pH on Vascular Tension : Which are the Important Mechanisms, J Vasc Res, 1996, PMID: 8862140, pp. 347-359, vol. 33(5), abs.

Johansson B, Myogenic Tone and Reactivity: Definitions Based on Muscle Phsiology, J Hypertens Suppl, 1989, pp. S5-S8, vol. 7(4), abs.

Javier F Aduen and Others, Blood Lactate Accumulation: Hemodynamics and Acid Base Status, J Intensive Care Med, 2002, pp. 180-185, vol. 17 No. 4, abs.

Robergs R and Others, Influence of Pre-Exerc Acisosis and Alkalosis on the Kinetics of Acid-Base Rcvery Following Int Exerc, Int J Sport Nutr Metab, 2005, pp. 59-74, vol. 15(1), abs.

C.W. Zwillich and Others, Effects of Hypocapnia and Hypocapnic Alkalosis on Cardiovascular Function, J Appl Physiol, 1976, pp. 333-337, vol. 40 Issue 3, abs.

Kazmaier S, Effects of Respiratory Alkalosis and Acidosis on Myocardial Blood Flow and Metab in Patients with Coronary Artery Disease, Anesthesiology, 1998, pp. 831-837, V89(4), abs.

Neill WA and Hattenhauer M, Impairment of Myocardial O2 Supplu Due to Hyperventillation, Circulation, 1975, pp. 854-858, vol. 52(5), abs.

John M. Kowalchuk and Others, Effect of pH on Metabolic and Cardiorespiratory Responses During Progressive Exercise, Dept. of Med, McMaster Univ Med Center, Hamilton, Ontario.

Hiroshi Ishizaka and Lih Kuo, Acidosis-Indcd Coronary Arteriolar Dilation id Mediated by ATP-Sens Potas Channels in Vascular Smooth Mscl, Circ Research, 1996, 50-7 vol. 78.

Xing-Guo Sun and Others, Carbon Dioxide Pressure-Concentration Realtionship in Arterial and Mixed Venous Blood During Exercise, J Appl Physiol, 2001, pp. 1798-1810, vol. 90.

L. B. Gladden, Lactate Metabolism: A New Paradigm for the Third Millinnium, J Appl Physiol, 2004, pp. 5-30, vol. 558.1.

Sabino Padilla, Scientific Approach to the 1-h Cycling World Record: A Case Study, J Appl Physiol, 2000, pp. 1522-1527, vol. 89.

Raymer et al, Tables, J Appl Physiol, pp. 2050, vol. 96(6).
Kohji Hirakoba and Takahiro Yunoki, J Physiol Anthropology, pp. 143-149.
L. Bruce Gladden, Lactic Acid: New Roles in a New Millennium, PNAS, 2001, pp. 395-397, vol. 98 No. 2.
Guidelines 2000 for Cardiopulmonary Rescitation and Emergency Cardiovascular Care, American Heart Assoc, 2000, vol. 102 No. 8.
William D McArdle and Others, Exercise Physiology, ISBN 0-7817-2544-5, Copyright 2001, pic.

Voopik and Others, Effects of Sodium Citrate Ingestion Before Exercise on Endurance Performance in Well Trained College Runners, Br J Sports Med, 2003, pp. 485-489, vol. 37.
International Search Report and Written Opinion of the International Searching Authority for International Application No. PCT/US07/01639, mailed Oct. 12, 2007, 8 pages.

* cited by examiner

METHOD FOR ENHANCED PERFORMANCE TRAINING

TECHNICAL FIELD

The present invention relates to the field of performance and exercise training, in particular, to a method of improved performance and exercise training by utilization of intentional controlled tachypnea and somatic sensory alkalosis biofeedback training.

BACKGROUND OF THE INVENTION

During physical activity, the energy demand of the human body greatly increases. Sustained exercise such as marathon running increases the whole-body energy requirement by 20-30 times over resting levels. The energy utilized to accommodate this demand, along with all other energy-requiring systems in the human body, comes in large part from the energy contained within ATP, adenosine triphosphate.

The most efficient, albeit slower, method of generating this ATP is under aerobic conditions, where oxygen is present and consumed. This method is named oxidation, or, the oxidative pathway. Different forms of fuel (e.g. proteins, fat, and carbohydrate) can be metabolized by oxidation to create ATP. The creation of ATP by aerobic means is typically favored by physical performance efforts of longer duration. The complete oxidation of one molecule of glucose yields up to 36 ATP molecules for skeletal muscle (38 for cardiac muscle).

As the intensity of effort increases, ATP is generated increasingly via another faster, but less efficient, pathway, anaerobic glycolysis, where glucose is metabolized to generate ATP (glycolysis) in the absence of oxygen (anaerobic). ATP is generated in the absence of oxygen only via anaerobic glycolysis. Being less efficient than oxidation, one molecule of glucose yields only 2 ATP molecules, far from the 36 obtained through oxidation. In addition, anaerobic glycolysis creates 2 lactic acid molecules for each glucose molecule metabolized. Increased use of the glycolytic system results in higher rates of glucose utilization, glycogen depletion, and lactic acid production.

The state of lactic acid is such that it dissociates almost totally into its ionized form resulting in lactate and a proton, or $H^+$ (hydrogen ion), as follows:

TABLE 1

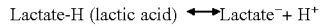

Lactate-H (lactic acid) ⇌ Lactate⁻ + $H^+$

Lactate itself may be metabolized by oxidation or converted to glucose or amino acids. In this way lactate may serve as a fuel substrate for work done by cardiac and skeletal muscle.

At lower levels of intensity and anaerobic glycolysis, the generation of every lactate molecule is matched by its removal/metabolism, and lactate does not tend to accumulate. Lactate will begin to accumulate, though, in untrained individuals when exercise reaches approximately 55 to 65% of their maximal capacity. Trained athletes, due to a combination of factors, are able to exercise at a higher intensity prior to the onset of lactate accumulation, at approximately 65 to 75% of maximal capacity. The intensity of effort at which this occurs for any given individual is designated that individual's blood lactate threshold. Beyond this limit, lactate begins to accumulate in the cellular environment followed by the measurable accumulation in the blood. The lactate threshold defines the onset of lactic acidosis, and also the onset of significant anaerobic glycolysis. The lactate threshold has been commonly defined as the highest oxygen consumption or exercise intensity resulting in at least a 1.0 millimolar (mM) increase in blood lactate level above the pre-exercise level.

As lactic acid levels rise the equation in Table 1 is directed to the right resulting in the generation of more $H^+$, or hydrogen ions. The concentration (expressed by use of the common notation: [ ]) of hydrogen ions in the blood, $[H^+]$, determines whether the blood is acidic (pH<7.35), alkaline (pH>7.45), or normal (pH 7.35-7.45). Therefore, as lactic acid levels increase, [H+] increases, acidity increases, and pH is lowered. Lactic acidosis is a specific and very common pathologic acid/base disorder under the more general grouping of "metabolic acidosis" disorders. During intense physical exertion the accumulation of lactic acid, i.e., lactic acidosis, is the major contributor to the development of a metabolic acidosis. With regards to exercise and performance, it is not lactate that impairs performance, but rather the acidosis, or $H^+$, component.

The bicarbonate ion ($HCO_3^-$) which is present in the blood is consumed as it buffers the lactic acid, or more specifically, the $H^+$, created during exercise producing lactate, water and carbon dioxide as in the reaction of Table 2:

TABLE 2

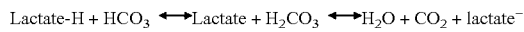

Lactate-H + $HCO_3$ ⇌ Lactate + $H_2CO_3$ ⇌ $H_2O + CO_2$ + lactate⁻

As a result, blood bicarbonate levels drop in the presence of lactic (or metabolic) acidosis. This neutralization process and state of equilibrium can be simplified as seen in Table 3:

TABLE 3

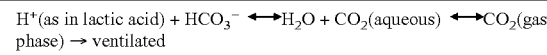

$H^+$(as in lactic acid) + $HCO_3^-$ ⇌ $H_2O + CO_2$(aqueous) ⇌ $CO_2$(gas phase) → ventilated As the bicarbonate buffers the lactic acid, $CO_2$ is generated in the aqueous phase. Aqueous $CO_2$ dissolves across the pulmonary alveolar capillary membrane into the alveoli, which is then expired out through the lungs. The process whereby $CO_2$ is expired and eliminated from the body is termed ventilation. The diffusion and elimination of $CO_2$ across the pulmonary capillary membrane into the alveolus is very fast—at a rate approximately 20 times that of oxygen, due to the significantly greater solubility of $CO_2$.

Table 3, when directed to the right, illustrates how blood acidity, or $[H^+]$, can be directly reduced by expiring, or ventilating, more $CO_2$. It is the most efficient method of reducing hydrogen ions in the body. Increasing ventilation will result in a decrease in acidosis, or alternatively, an increase in alkalosis.

Using the current art, during exercise, absent the appearance of lactic acid, ventilation would otherwise increase in a linear manner with increasing exercise in order to provide normal oxidative cellular respiration, i.e., to supply needed oxygen and to clear metabolic waste products, including $CO_2$. The excess $CO_2$ created as a result of the buffering of lactic acid by bicarbonate is referred to as "non-metabolic $CO_2$." This non-metabolic $CO_2$ represents an additional $CO_2$ load imposed on the body beyond that of normal cellular respiration. Rising $CO_2$ levels and acidosis are both potent stimulants of the brain's respiratory center and the human body responds with an autonomic, or involuntary action—increasing ventilation. In response to the appearance of lactic acid and new, non-metabolic, $CO_2$ there is an involuntary, abrupt and measurable increase in ventilation over that which would be expected to satisfy normal cellular respiration.

This increase in ventilation is termed compensatory, as it represents a reflex physiologic adaptive response to an acute acid/base disorder, specifically, lactic acidosis. Its purpose is to maintain $CO_2$ and thus, pH values, at a constant and normal level. The term ventilatory threshold (VT) is used to describe the point at which pulmonary ventilation begins to disproportionately increase in order to maintain normal $CO_2$, and thus, pH, levels. The ventilatory threshold can be illustrated as seen in FIG. 1.

Ventilation may also be compared with corresponding blood levels of arterial $CO_2$ and pH, as seen in FIG. 2. As a result of the compensatory increase in ventilation, pH, and alveolar, or arterial $CO_2$ levels remain within normal limits.

Indeed, multiple acid/base disorders commonly co-exist. Most commonly, there is a single acid/base disturbance followed by a compensatory response. The final acid/base status reflects where the net balance of the equation seen in Table 3 lies. If there is an increase in the [$H^+$], as would occur with lactic acidosis, the equation is directed to the left. Compensation for any acid/base disturbance is achieved by directing the equation in the opposite direction. In the case where [H+] increases, compensation would be to increase $CO_2$ output. In this fashion, if more $CO_2$ were eliminated than $H^+$ generated, the net effect would be a net decrease in the [$H^+$], i.e., a decrease in acidosis, or, increase in alkalosis. If this were achieved by respiratory means, e.g., by voluntarily and intentionally increasing ventilation, the process would be summarized as a metabolic acidosis with a compensatory respiratory alkalosis.

Thus, in exercise, the ventilatory threshold represents, in general, the onset of: 1) significant anaerobic glycolysis, 2) decreasing bicarbonate levels, 3) lactate accumulation, 4) metabolic, or, lactic acidosis, and 5) a compensatory respiratory alkalosis. As at all times during exercise or performance, the final pH of the blood will depend on where the balance of Table 3 will lie, that is, where the final balance between $H^+$ accumulation and $CO_2$ ventilation/elimination lies. Using the current art, pH and $CO_2$ levels remain unchanged as the ventilatory threshold is passed.

In exercise using the current art, as the intensity of effort increases beyond the ventilatory threshold, the generation of lactic acid escalates. The generation of $H^+$ eventually overwhelms the ventilation of $CO_2$ and there is an overall net increase in the [$H^+$], i.e., Table 3 is directed to the left. While up until this point blood pH has been normal, when the balance tips to the extent such that the net increase in [$H^+$] equates to a blood pH of 7.35, the blood finally becomes, by definition, measurably acidic. In the current art, the point where this measurable acidosis (pH<7.35) starts is termed the Point of Metabolic Acidosis (PMA). Synonymous terms for this transition point are the Respiratory Compensation Threshold (RCT) or the Onset of Blood Lactate Accumulation (OBLA); however, PMA shall be preferentially used throughout this specification. With the onset of systemic acidosis, there is a cascade whereby any further increase in effort is met with exponentially decreasing efficiency. With increasing effort, lactic acid, and $H^+$, accumulate in an accelerating fashion and the blood becomes increasingly more acidic. Concomitant with the PMA is another disproportionate compensatory increase in ventilation—with arterial $CO_2$ values becoming similar to those values seen in hyperventilation.

At the PMA, increasing ventilation is done in an effort to drive the balance seen in Table 3 to the right in the face of a measurable acidosis. This is ineffectual and the [H+] continues to increase. The net direction of the balance seen in Table 3, despite maximum efforts in ventilation and trying to direct the balance seen in Table 3 to the right, is to the left. As the equation drives to the left, more $CO_2$ is consumed in order to generate $HCO_3^-$ to buffer the $H^+$ and the end result is a net loss of $CO_2$. A summary of these changes can be illustrated as seen in FIG. 3.

To understand the instant invention, though, one must look closer, specifically, to the area around the ventilatory threshold and the PMA. While blood pH and arterial $CO_2$ measurements may be stated to be normal up until the PMA, there will still be measurable changes both in pH and partial pressure of $CO_2$ ($pCO_2$) despite levels remaining in established normal limits. Firstly, as it is known that ventilation was stimulated by a change in $pCO_2$ and/or pH, there must have been a change to begin with. Secondly, there must be some travel from a normal resting average for blood pH, e.g. a pH of 7.4, down to the lower limits of normal, in the case of blood pH, 7.35. Both of these factors lead to the conclusion that there is a relative increase in acidosis, or decrease in alkalosis, even prior to the onset of a measurable abnormality. Indeed, it should be interpreted that there is a net shift in Table 3 to the left and the net accumulation of $H^+$, i.e., an increase in acidosis or a decrease in alkalosis, following the ventilatory, or, lactate, threshold. Magnified, pH and $pCO_2$ values between the ventilatory threshold and the PMA of FIG. 3 would appear as seen in FIG. 4. It is important to note that measurable changes in pH can occur as a result of very small changes in $pCO_2$ levels.

The PMA is generally regarded as occurring around a lactate concentration of 4 mmol/L. Following this, there is a sharply decreasing ability to generate an increase in performance. Although there is considerable variability among individuals, the intensity of effort around the PMA is also thought to approximate the maximum exercise intensity that a person can sustain for a prolonged duration (in general, though, higher lactate levels, in the range of 7 or 8 mmol/L, can be tolerated for varying periods of time). For elite athletes, this lies around 75-90% of their maximum heart rate or oxygen consumption, and less than these values for more novice athletes and untrained individuals. Using the current art of exercise training, the popular term given to this approximate level, i.e., PMA, although possibly a misnomer, is that athlete's lactate, or anaerobic, threshold. This author intentionally excludes any reference to the PMA as being approximate to an individual's lactate or anaerobic threshold. Lactate threshold will continue to be defined as that level of oxygen consumption, heart rate, exercise intensity etc. at which there is a measurable increase in systemic lactic acid levels e.g. at least a 1.0 millimolar (mM) increase in blood lactate level above the pre-exercise level Acidosis is one of, if not the most important determinants of maximal performance during intense athletic exercise. Acidosis is well known to adversely affect immediate muscle performance. Any systemic acidosis created by inefficient ventilation negatively affects cellular metabolism and the contractile capacity of active muscles. Deleterious effects of acidosis can be cumulative and chronic, lasting days, weeks, months etc.

In addition to the direct effects of acidosis on physiological performance, indirect effects also occur. For example, diaphragmatic function is impaired during acidosis, but not during alkalosis, leading to less efficient respiration and ventilation. Acidosis can lead to higher intra-muscular compartment pressures. This may be accompanied by muscle soreness, with indices of muscle damage, such as elevated CPK, LDH, and myoglobin, becoming measurable. The mechanism of this acute and chronic muscle damage phenomenon may be multi-factorial, but acidosis is likely a significant contributor.

Acidosis also leads to impaired hemodynamics. Indeed, macroscopic increases in muscle size following exercise are measurable by ultrasound. As muscle groups are typically bounded in closed compartments, an increase in compartmental volume leads to an increase in compartment pressure. Elevated compartment pressures will negatively affect the smallest and weakest vascular beds such as the smaller end-branch arterioles, arterio-venous capillaries, and venules, i.e., those vascular beds already carrying the least amount of oxygen. All of these mechanisms perpetuate and exacerbate oxygen delivery, $CO_2$ clearance, and subsequently, acidosis.

Ventilation is an essential, but underutilized component of exercise. There is evidence that humans possess considerable respiratory, and hence, ventilatory reserve during strenuous physical activity, with this reserve estimated to be between 15% and 40% of a healthy person's maximum voluntary ventilation.

In the prior art, the control of respiration has been left to a passive, intrinsic, and involuntary system that operates through a number of reflex feedback mechanisms, with $CO_2$ levels and pH being large determinants. However, the considerable respiratory reserve available in most instances indicates that there is physiological room for considerable voluntary manipulation of respiration.

By utilizing the considerable respiratory reserve presently unused, one can affect a net drop in $CO_2$ despite rising lactic acid levels, that is, by increasing ventilation relatively early during exercise, to create a systemic alkalosis reserve. By these means, acidosis can be eliminated along with its concomitant detrimental effects.

A systemic alkalosis is preferred or at least a neutral systemic pH during exercise or performance as alkalosis itself is known to enhance performance. There is current evidence that performance is enhanced during the state of metabolic alkalosis. Instead of creating a systemic alkalosis via compensatory ventilatory changes, buffering is accomplished via metabolic means, that is, through ingestion of an alkaline drink such as sodium bicarbonate or calcium citrate. The effects of such treatment are, unfortunately, short lived and, contrary to its intent, may lead to a paradoxical increase in cellular acidosis. This effect is not surprising given the buffering equation of Table 3. With a net increase in bicarbonate (ingested) the equation in Table 3 is directed to the left leading to an increased production of free hydrogen ions ($H^+$), and therefore, more acidosis. This paradoxical increase in acidosis is well known to those medical personnel performing emergency resuscitation using Advanced Cardiac Life Support (ACLS) guidelines. Bicarbonate is no longer recommended as routine treatment in cardiac arrest as it leads to the development of a paradoxical acidosis.

In addition, it has also been reported that intracellular pH is unaffected by ingesting $HCO_3^-$ and that its benefits are obtained from the extracellular alkalosis alone. This has lead to the hypothesis that the cellular membrane is impermeable to $HCO_3^-$ molecule.

Ventilation of $CO_2$ is the single most effective way of decreasing intracellular and mitochondrial levels of $CO_2$, with alveolar $CO_2$ levels being nearly equivalent to that of the intracellular and mitochondrial $CO_2$ levels, where ATP is generated. The greater the quantity of $CO_2$ ventilated, the lesser the quantity of $CO_2$ remaining in cells and mitochondria. This leads to a decrease in intra-cellular/intra-mitochondrial acidosis, or increase in alkalosis. In contrast to the ingestion of $HCO_3^-$ and its resultant metabolic alkalosis, the mitochondrial pH can be altered via ventilation, specifically by maximizing $CO_2$ ventilation.

Until recent times, difficulties in obtaining real-time measurement of blood $CO_2$ levels precluded effective techniques in the management of respiration. Traditionally, arterial $CO_2$ could only be measured after an invasive and complicated procedure such as the collection of an arterial blood sample by arterial puncture. Similarly complicated and inconvenient efforts are required to approximate blood $CO_2$ levels after collection of expired (alveolar) $CO_2$. The necessity for cumbersome or invasive equipment essentially precluded regular or routine measurement in an exercise setting. However, the availability of transcutaneous $CO_2$ monitoring allows direct real-time monitoring of blood $CO_2$ levels, during exercise, and can be used to assist in creating a feedback loop method of the instant invention that instructs the athlete in means to maximize both the efficiency of respiration and total amount of $CO_2$ expired both before and during athletic performance.

SUMMARY OF INVENTION

In its most general configuration, the present invention advances the state of the art with a variety of new capabilities and overcomes many of the shortcomings of prior methods in new and novel ways.

Prior art attempts to improve athletic performance focus on various training regimens geared to improving skeletal muscle performance. It is presently thought that present maximal athletic efforts are limited by muscular exhaustion. Muscular exhaustion is typically heralded by the interpretation or perception of a crescendo pattern in muscular pain and dysfunction. Maximal athletic efforts, though, are also associated with respiratory fatigue and exhaustion typically interpreted or perceived as uncontrolled exhaustive hyperventilation. Both are related to the metabolic acidosis caused by the accumulation of lactic acid generated from exercising muscle. The instructional strategy and methods of the instant invention show that the present limits in onset of acidosis are not inevitable in human performance and that muscular exhaustion does not exclusively limit maximal performance. The results of these methods illustrate two important shifts in the understanding of performance limitations. First, is the discovery that acidosis is more preventable during exercise than previously thought. The second is the discovery that maximum efforts can be enhanced via augmented respiratory methods.

Transcutaneous monitoring of carbon dioxide ($TCO_2$) is a novel and essential tool to enhance athletic performance. $TCO_2$ levels are monitored as a feedback mechanism for the athlete to induce an early and enhanced respiratory alkalosis, which is created to compensate for the metabolic acidosis caused by the unavoidable and progressive accumulation of lactic acid generated by exercising muscle. Using the $TCO_2$ monitor allows an effective focus to be placed on ventilation—the elimination of $CO_2$, to create a relative systemic alkalosis. A systemic alkalosis, or at least a neutral systemic pH, is preferable at all times during exercise. Through further manipulation of an individual's $CO_2$ ventilation, the athlete also becomes capable of enhancing the body's available alkaline reserve, in essence, 'building' upon the state of alkalosis thereby enabling a greater acid buffering capacity. Because greater lactic acid levels become tolerable with the presence of an improved compensatory systemic alkalosis (buffering this rise in lactic acid), the individual is allowed to increase the intensity of effort more efficiently compared to equivalent intensities in the acidotic state. Performance efficiency declines rapidly in an acidotic state.

This respiratory/ventilatory compensation is directed not only to maximal efforts but also throughout a broad spectrum of performance or activity intensities and situations ranging from day-to-day training or activity, immediate pre-performance preparation, or to efforts of maximal intensities; be they of short or prolonged duration.

With the use of $TCO_2$ monitoring, the athlete is taught to recognize the most subtle somatic sensations associated with the onset of acidosis. Currently, the somatic sensations of acidosis are most identifiable as the athlete nears maximal efforts—hence the aphorism "No pain, no gain." The onset of acidosis, though, is much earlier and correlates roughly with the lactate threshold. With the aid of $TCO_2$ and heart rate monitoring, the athlete is enlightened to recognize the benefit of a systemic alkalosis, even while at the earliest onset of acidosis, i.e., the lactate threshold, when arterial and venous blood pH is neutral. In the instant invention, no effort is made to alter lactate concentrations. Rather, the goal is to eliminate acidosis.

Around the earliest stage of acidosis the athlete is instructed to increase ventilation. From this point on, the instant invention trains the athlete to progressively lower $TCO_2$ levels as effort and intensity increases. This change in ventilation results in a systemic alkalosis of varying degree. The effect of ventilation is proportional to the athlete's effort. The greater the ventilatory effort, the greater the compensatory alkalosis. In this fashion, the individual is able to 'tap' into an available 'alkaline reserve'. The instant invention teaches the athlete to realize the benefit of systemic alkalosis throughout a broad spectrum of intensities, from the lactate threshold, up to and including maximum and supra-maximal efforts. The athlete maximizes his or her ability to lower $TCO_2$ levels, i.e., to maximize the amount of $CO_2$ expired, while performing maximum efforts for prolonged periods of time.

Another novel aspect of the instant invention is to train individuals to optimize a systemic alkalosis or alkaline reserve that would be used in anticipation of a known, upcoming intense, maximal effort, for example, immediately prior to the start of a race, or prior to an upcoming obstacle during a race, such as a hill that must be climbed. In these cases, the athlete is taught to increase and maintain maximum ventilation to a point just shy of hyperventilation to create an optimum systemic alkalosis or alkaline reserve. This alkalosis is then utilized to compensate for the sudden surge of lactic acid, or acidosis, expected from the upcoming intense effort.

This change in respiratory effort is correlated closely with somatic muscular symptoms, such that pain, swelling, and dysfunction are avoided. True maximal performance is heralded by the precipitous appearance of acidosis and its related symptoms, and a subsequent steep and rapid decline in performance. In this fashion, in the instant invention, maximum effort is limited by respiratory ability, that is, when it is no longer able to buffer increasing levels of lactic acid through maximum ventilation.

Another novel benefit of the instant invention is the creation of a training system to prolong breath-holding while performing strenuous exercise. The stimulus to breathe can be blunted with the creation a systemic hypocarbic alkalotic state, the inverse of the effect occurring with hypercarbic acidosis and its stimulation of breathing. This technique would be invaluable and potentially life-saving to an athlete such as a kayaker or surfer who is required to breath-hold following underwater immersion.

$TCO_2$ monitoring is also effective in monitoring muscular fatigue and recovery from racing or training. During the earliest stages of fatigue or overtraining, somatic signals may not be detected by an individual. In this fashion fatigue can be detected by higher resting $TCO_2$ levels. Delayed lowering and diminished absolute drops in $TCO_2$ during any performance intensity are additional indicators of muscle fatigue and incomplete recovery. Appropriate measures can be made to alter training or performance intensity so as to resolve this potentially detrimental and injurious physiologic state.

These variations, modifications, alternatives, and alterations of the various preferred embodiments may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures:

DETAILED DESCRIPTION OF THE INVENTION

The method of the instant invention enables a significant advance in the state of the art. The preferred embodiments of the method accomplish this by new and novel arrangements of elements and methods that are configured in unique and novel ways and which demonstrate previously unavailable but preferred and desirable capabilities. The detailed description set forth below in connection with the drawings is intended merely as a description of the presently preferred embodiments of the invention, and is not intended to represent the only form in which the present invention may be practiced. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

The present invention is a method for enhanced transcutaneous carbon dioxide ($TCO_2$) control exercise training; including a controlled breathing method for increasing an alkaline reserve of an individual, and a technique for teaching controlled breathing for maximizing breath holding time of an individual; by utilization of intentional controlled tachypnea and somatic sensory alkalosis biofeedback training.

Respiration is delineated into two phases. The first is the inhalation, or oxygenation, phase, which serves to provide a sufficient quantity of oxygen to meet the metabolic demands of the body. The second is the expiratory, or ventilation, phase, whereby $CO_2$, the metabolic waste product of normal cellular function, is eliminated.

Hypoxia is defined as the presence of insufficient amounts of oxygen in the blood or tissue. Typically, under normal athletic performance conditions, arterial oxygen saturation levels remain above 90% ($SaO_2$>90%) even at maximal efforts. This amount of oxygen is sufficient even for maximal performance. Therefore, hypoxia is not the limiting factor in maximal performance. Regardless, the fractional concentration of oxygen present in the atmosphere remains fixed (approximately 21%), and there is a limited ability of the pulmonary system to extract greater amounts of oxygen into the systemic circulation. While certain physiologic manipulations, such as the use of EPO (erythropoietin), a hormone that stimulates the production of red blood cells by bone marrow, can increase oxygen content in the blood, such manipulations are considered highly unethical in the sports community.

Figure 1:
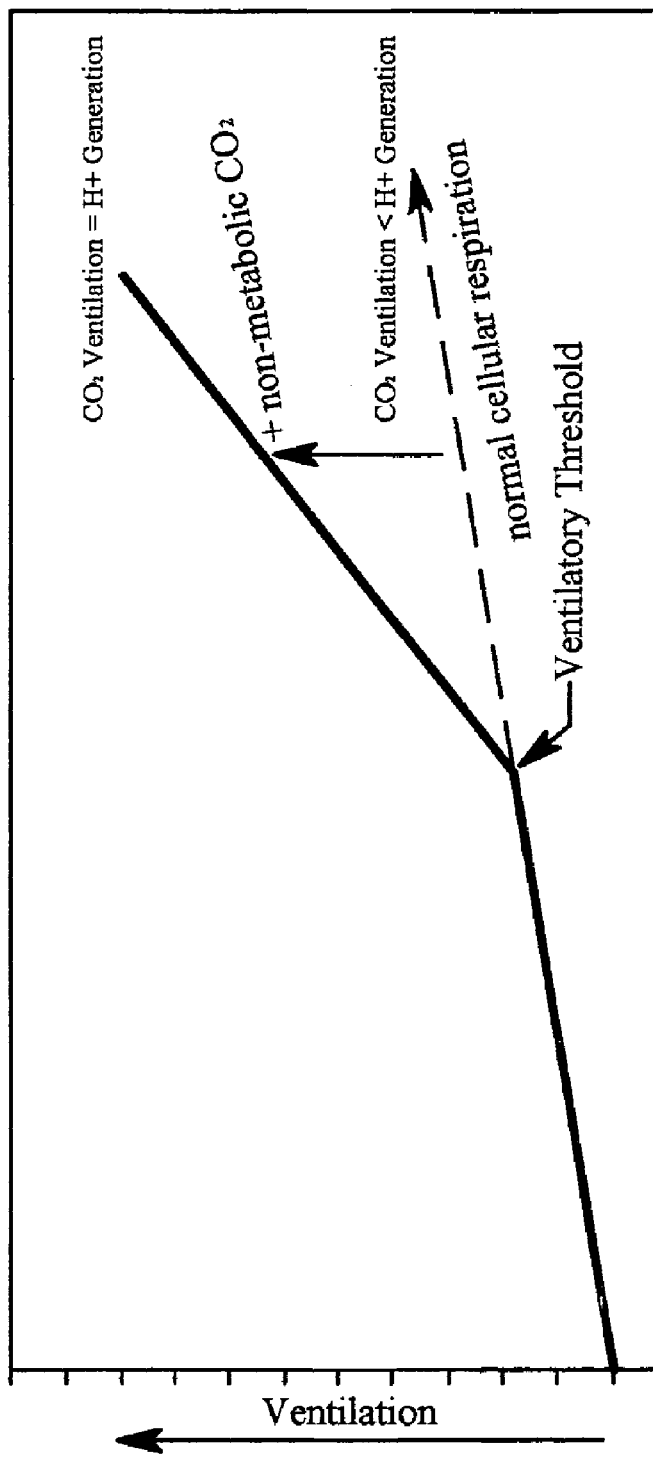
FIG. 1 shows ventilation as a function of oxygen consumption and intensity of effort, showing the increase in non-metabolic $CO_2$ over that produced by normal cellular respiration found at the ventilatory threshold.
Figure 2:
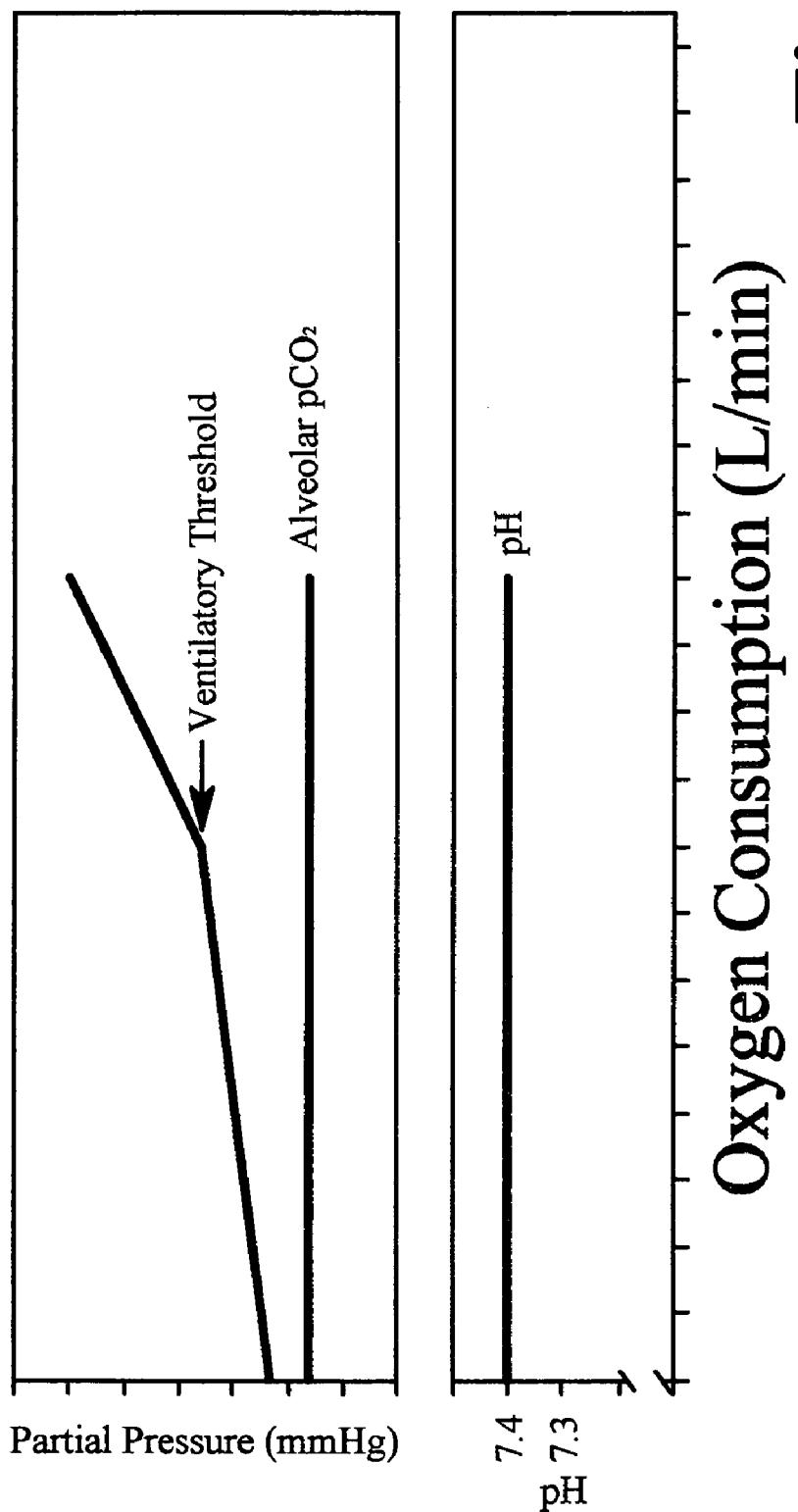
FIG. 2 shows the relationship between ventilation, alveolar $PCO_2$, and blood pH, as oxygen consumption is increased beyond the ventilatory threshold but before the PMA.
Figure 3:
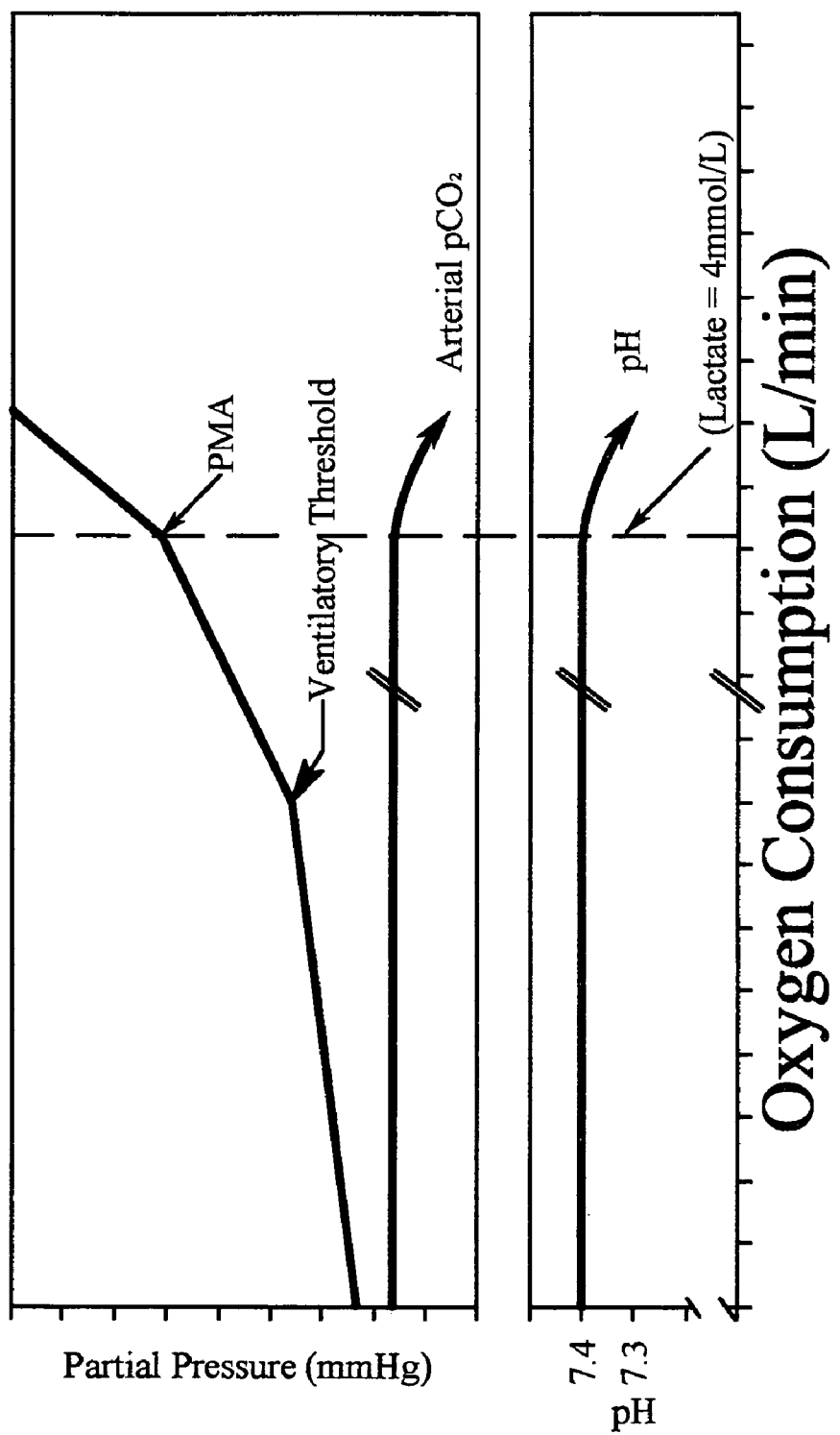
FIG. 3 shows the relationship between ventilation, arterial $pCO_2$, and blood pH, as oxygen consumption is further increased over that Shown in FIG. 2, as seen in increased intensity exercise, particularly showing the fall in arterial $PCO_2$, and blood pH following the PMA.
Figure 4:
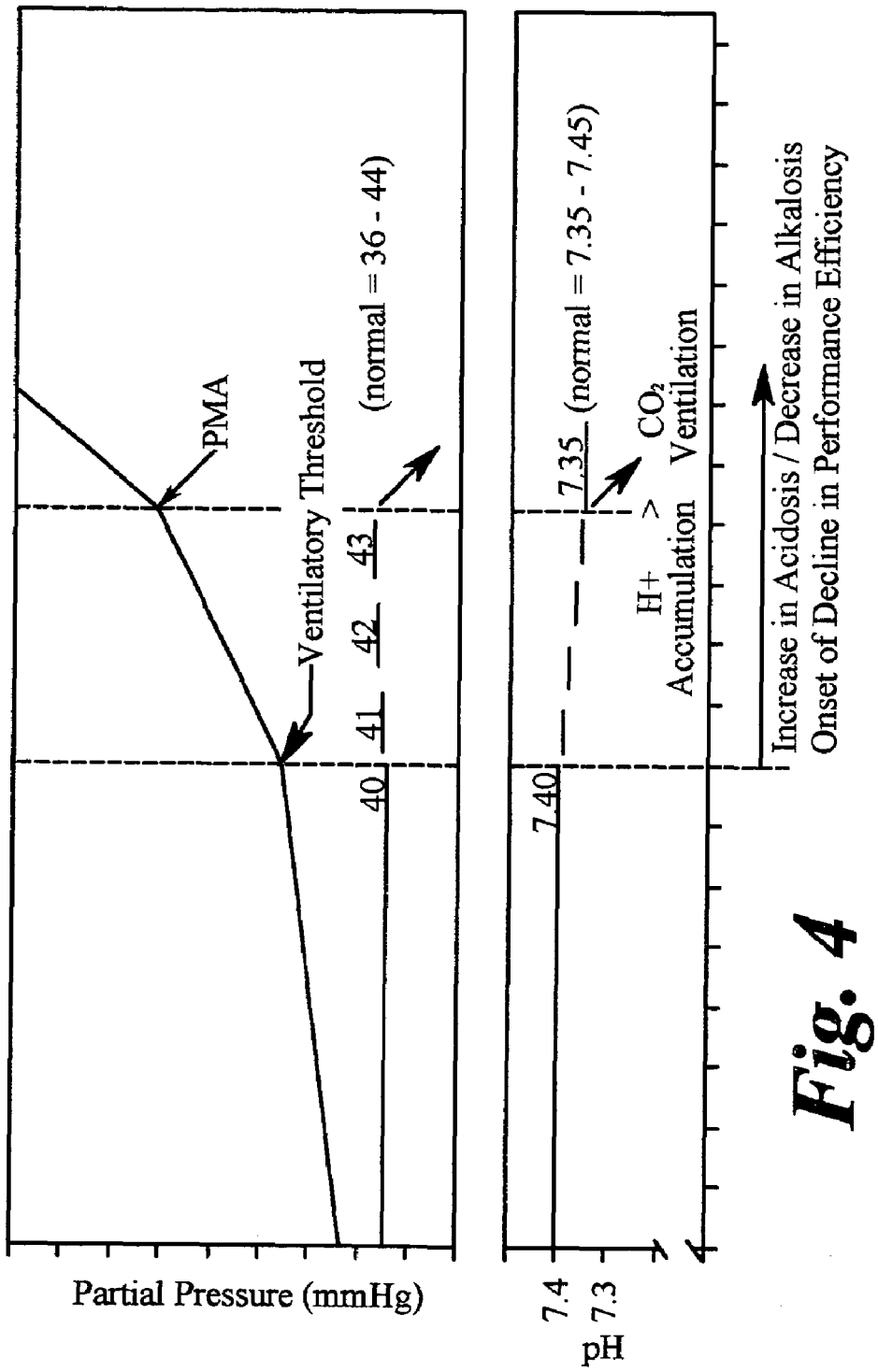
FIG. 4 shows the relationships of FIG. 3 in greater detail, illustrating the progress rise in arterial $pCO_2$, and fall in blood pH associated with exercise beyond the ventilatory threshold followed by the simultaneous decline in both arterial $pCO_2$ and pH following the PMA, representing the progressive failure to respire sufficient $CO_2$, to compensate for increased $H^+$ production.

Arterial blood gases, that is, the measurement of gas levels in the blood as sampled in the arteries, do not accurately reflect the cellular environment. The cellular environment can be hypoxic despite normal arterial oxygen partial pressures and saturation. McCardle estimates that the partial pressure of oxygen in fluid around the muscle cell at rest is around 40 mm Hg. With strenuous exercise, however, the partial pressure of oxygen around muscle cells falls toward 0 mm Hg. As a result, muscle will generate energy in an anaerobic environment via anaerobic glycolysis with the by-product of lactic acid. As intensity increases, the balance between supply and demand is further altered. With a limited supply of oxygen and progressively increasing intensity of effort, more and more oxygen is extracted by the demanding muscle tissue leaving less and less oxygen available to those muscle cells most distant from the blood supply. There exists a spectrum in the cellular environment where, as intensity increases, oxygen extraction by the muscles increases, thereby increasing the total hypoxic environment. This leads to the generation and accumulation of increasing amounts of lactic acid and non-metabolic $CO_2$ into the systemic circulation. This cycle is illustrated in FIG. 4. The increasing $CO_2$ values seen in FIG. 4 are illustrative only, intending to show a slight rise in $CO_2$ with exercise and $CO_2$ levels remaining within normal range.

Under normal circumstances, arterial $pCO_2$ levels are in the range of 36-44 mm Hg, and typically around 40 mm Hg in the resting state. Hypocapnia (or hypocarbia) is defined as a $pCO_2$ level below that considered normal, typically less than 36-40 mm Hg. The measurement of $CO_2$ levels through the skin, that is, transcutaneous levels ($TCO_2$) are considered equivalent to arterial $pCO_2$ values during exercise.

Respiratory alkalosis is defined as the presence of an alkalemia (i.e., blood present in an alkaline pH, or pH>7.45), due to respiratory changes, rather than metabolic changes (as in the ingestion of sodium bicarbonate), with subsequent hypocapnia. Indeed, a net drop in $CO_2$ levels must be seen if an alkalosis is to be created via respiratory means, with ventilation being increased and a disproportionate excess of $CO_2$ being ventilated and eliminated.

Using the training techniques of the instant invention, hypocapnia can be controlled to a degree that is inversely proportional to the ventilatory effort. The resultant alkalotic, or at least neutral, pH state is preferable to the presence of acidosis which occurs in exercise using the present art.

Figure 5:
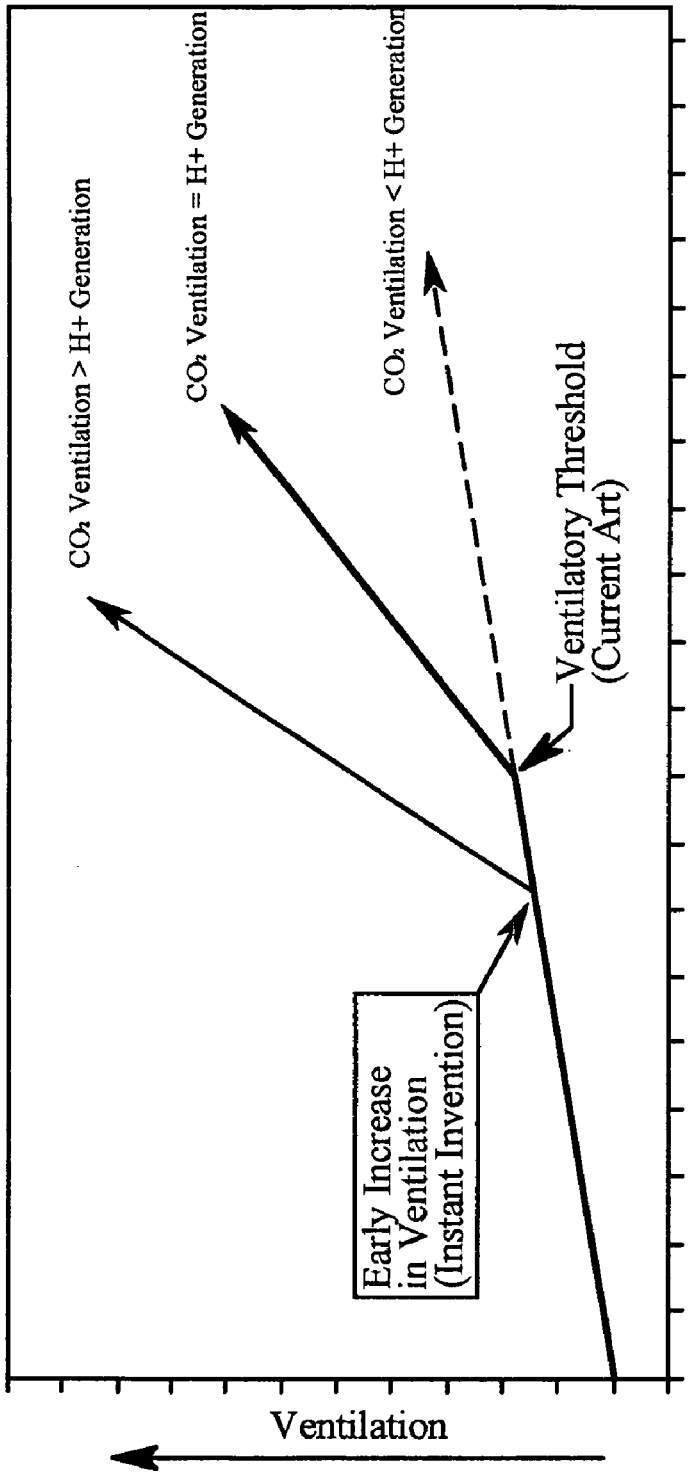
FIG. 5 shows ventilation as a function of oxygen consumption and intensity of effort, showing how the early increase of ventilation of the instant invention increases $CO_2$, ventilation to compensate for increased $H^+$ production such that there is a net loss of $H^+$.

With the instant invention, respiratory "over-compensation" to the point of alkalosis is attained prior to the measured lactate threshold. This early compensatory effort is in contrast to the late compensatory effort in the current art. In the instant invention, the athlete must initiate an increase in his breathing, or, more specifically, ventilation, to affect an early drop in $TCO_2$ levels so that the end result is an alkalosis. This is illustrated in FIG. 5.

The difference between the respiratory effort an athlete uses at present to perform at a desired athletic level and the maximum respiratory capability is the exertional respiratory reserve. Accessing this respiratory reserve using the instant invention, can offer an additional 15-40% improvement in performance, using essentially the maximum ventilation an individual is capable of. Using the instant invention allows an athlete to expire greater quantities of $CO_2$ and reduce acidosis during any effort. A key assumption underlying the accessing of this reserve is that an athlete must no longer allow normal physiological respiratory reflexes to stimulate or control respiratory rate or effort. In short, this passive, involuntary process is made to become a voluntary, active, intentional process.

Figure 6:
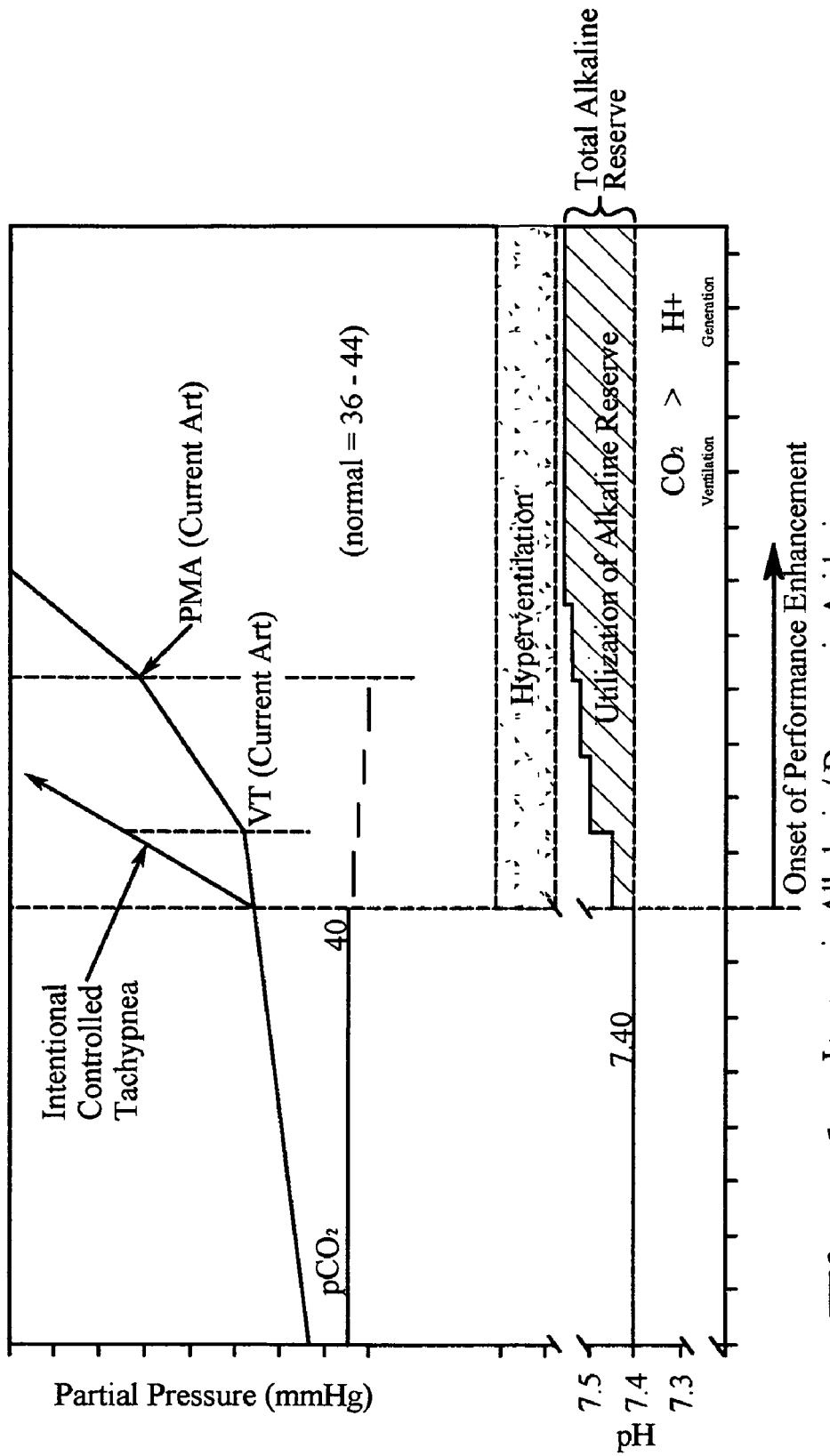
FIG. 6 shows the relationships of FIG. 5 in greater detail, illustrating how the early increase of ventilation of the instant invention increases $CO_2$, ventilation and thereby creates an enhanced alkaline reserve to compensate for increased $H^+$ production.

This intentional phenomenon is defined herein as Intentional Controlled Tachypnea (ICT) during exercise. The changes seen using the instant invention can be illustrated as seen in FIG. 6. As can be seen, increasing ventilation along the line labeled "Intentional Controlled Tachypnea" (ICT) in FIG. 6, creates a lowering of $TCO_2$ levels and an increase in alkalosis. Tachypnea is defined as rapid breathing, or an increased rate of breathing. ICT during exercise may focus on an infinite number of variations in respiratory patterns. Each pattern must be individualized through controlled experimentation. Strategies include combinations of, but are not limited to: Increasing respiratory rate; increasing forced expiration so as to expire higher concentrations of $CO_2$ present in the alveoli and pulmonary physiologic dead space; and increasing inspiratory volume so as to increase alveolar surface area. An increase in alveolar surface area not only increases the surface area over which oxygen may diffuse into the body (thus maximizing the amount of oxygen that is delivered to the tissue), but it also increases the surface area over which $CO_2$ may diffuse into the airspace for expiration and elimination. In this respect, deep inspiration should be considered essential not only to maximize oxygen intake, but also to augment $CO_2$ elimination.

Intentional controlled tachypnea must be differentiated from hyperventilation syndrome. Hyperventilation syndrome is a syndrome whereby ventilation, i.e., the elimination of $CO_2$ from the body, exceeds metabolic demands. The end result is a constellation of symptoms, physical findings, hemodynamic changes and metabolic derangements that could adversely affect the immediate health of the individual. This pathological process occurs secondary to the creation of an acute and rapid uncompensated respiratory alkalosis. Even while exercising near maximal efforts it is still possible to develop this pathological syndrome, that is, to hyperventilate near maximal effort. Care and supervision must be undertaken so as not to push ventilation to the point of inducing this syndrome and its accompanying problems when performing ICT.

A useful exercise to assist a trainee in avoiding hyperventilation syndrome is to give the trainee a brief experience of the earliest symptoms of hyperventilation syndrome in order that he or she will know what symptoms herald the onset of hyperventilation syndrome. This may be done by asking the trainee, while at rest, to take six quick, deep breaths. This will often produce a slight dizziness, or dissociated, dysphoric feeling due to the rapid loss of $CO_2$. The trainee will then know, that in the event of the occurrence of these symptoms, he or she should decrease their ventilation.

In the exercising athlete, hyperventilation would be differentiated as exertional hyperventilation where ventilation during exertion exceeds the metabolic demands required by that given level of exertion. Hyperventilation syndrome is typically referred to as a pathological state, when it causes the development of adverse symptoms such as those given above. It is characterized by respiratory alkalosis. However, as will be shown, a slight respiratory alkalosis during exercise can be tolerated and maintained without the concomitant adverse effects of Hyperventilation Syndrome.

In the prior art, no effort has been made to directly correlate $CO_2$ levels, and thus pH levels, with detailed and subtle somatic symptoms. However, broad and generalized somatic symptoms have been described and measured during experimentation in exercise using the current art, with and without the ingestion of sodium bicarbonate, and the subsequent creation of a metabolic alkalosis. In such experimentation, not only was performance measurably enhanced during alkalosis, it was also associated with a diminished overall perception of exertion (PEO).

With the use of $TCO_2$ and heart rate monitoring, the goal of controlled alkalosis can finally be accomplished. While there are no presently documented objective measures of somatic responses at the lactate threshold, the athlete can utilize relative somatic sensations. The athlete can be taught to realize the relative change in somatic sensation as $TCO_2$ levels are intentionally dropped while around or above, the lactate threshold. For example, the athlete is instructed to increase intensity to a heart rate known (from previous blood sampling) to approximate the lactate threshold. The $TCO_2$ level is then intentionally dropped using ICT. The athlete is asked to focus on the somatic changes perceived as a result of this maneuver.

Certain symptoms are well known to be related to the transition to, acquisition of, and maintenance of an acidotic state including, but not limited to; loss of musculoskeletal coordination, disproportionately high sensory input from the working muscle(s), disproportionately high mental focus on working muscle(s), increase in burning sensation, and increase in pain in working muscle bed(s). There may also be a sensation of swollen or swelling in working muscle bed(s), an increase in overall sensation of cranial pressure, an increase in air hunger, an increase in anxiety, an increase in general irritability, an increase in perception of difficulty in task being performed, and prolonged symptomatology of pain/injury lasting hours after the performance or becoming chronic and long-lasting.

Other symptoms are known to be related to the transition to, acquisition of, and maintenance of an alkalotic state, including (but not limited to); improved musculoskeletal coordination, a decrease in sensory input from the working muscle(s), absence of pain, shrinking of tissue bed(s) in working muscle(s), cool temperature sensation especially in working muscle(s), blunting of respiratory drive, and a loss of air hunger. There may also be an increase and/or improvement in ability for deep and focused concentration, an increase and/or improvement in state of calmness, an increase and/or improvement in perception of ease related to task being performed, and an absence of or decrease in duration of persisting pain/injury following performance/training. Part of these benefits may be the result of an enhanced response to catecholamines, the 'fight or flight' hormones, as it is known that catecholamine sensitivity is impaired during acidosis and enhanced during alkalosis.

Once the individual is able to correctly interpret somatic sensations of acidosis versus alkalosis, he/she is guided through the exercise of progressively lowering $TCO_2$ levels as intensity of effort increases, at all times cognizant of the presence or absence of somatic signals of acidosis or alkalosis or hyperventilation syndrome, the goal being alkalosis or at least neutral pH near maximal efforts. The individual is then taught how to not only maintain a lowered $TCO_2$ level for the purpose of performance enhancement but also how to manipulate lowered $TCO_2$ levels to maximize alkaline reserve by establishing the lowest beneficial $TCO_2$ level for any given intensity. In this way, $TCO_2$ can serve as a tool for performance biofeedback during instruction and/or training. Intensity of effort can be guided by the heart rate. This improvement can be recognized at heart rates above and below the lactate threshold. Thereafter, when $TCO_2$ monitoring is not practical, the increase in ventilation becomes proportional to the athlete's perceived intensity of somatic sensations of acidosis or alkalosis. One particularly useful symptom that indicates the extent of a hypocarbic, alkalotic state is the duration of breathe-holding during any given level of performance intensity. One can assume that a greater alkalosis will result in a longer duration of breathe-holding.

The purpose of utilizing $TCO_2$ monitoring for the purpose of performance enhancement, is, first, to instruct the athlete on how to create an early and enhanced compensatory respiratory alkalosis using intentional controlled tachypnea and then, second, how to increase ventilation as intensity of effort increases, building or maintaining alkaline reserve. The goal is to guide the athlete to the point where acidosis no longer exists at maximal and supra-maximal efforts.

$VO_2$ is defined as the measurement of oxygen uptake during any given level of performance intensity, typically expressed in liters/minute, and $VO_2$max as the maximum amount of oxygen consumed during maximum efforts. $VO_2$max is often used as an indication of performance ability with higher values indicating greater fitness. With the aid of various methods of athletic training $VO_2$max can be increased, thereby allowing the athlete to sustain higher workloads over a given period of time.

$VCO_2$ is defined as the measurement of $CO_2$ expired during exertion at any given level of intensity and $VCO_2$max as the maximum volume of $CO_2$ expired during maximal efforts. $VCO_2$ and $VCO_2$max can be augmented beyond current limits through ICT. While performing $VCO_2$max over a prolonged period of time the individual is able to create a maximum compensatory respiratory alkalosis. In this fashion, the athlete can continue to increase intensity beyond currently established limits, as he or she will be able to withstand and progress through higher levels of intensity and lactic acidosis. Therefore, by tapping into a previously unavailable Exertional Respiratory Reserve via Intentional Controlled Tachypnea, $VCO_2$max is optimized. $VCO_2$max is an essential measurement and tool to help determine an athlete's true performance limit.

$TCO_2$ monitoring can also be used to instruct the athlete on how to maximize the systemic alkalosis that an athlete would require immediately prior to the start of a race or to an anticipated, upcoming intense physical effort. This effort can be sporadic during an endurance race, as it is assumed that the athlete may not be ventilating near maximum values at all times, as such would require an unnecessary and inappropriately large amount of focus or concentration. As the exercise duration shortens, though, maximum ventilating efforts may be required for the entire duration of the event. As mentioned above, there are no presently documented symptoms known to correlate with progressively declining arterial $CO_2$ concentrations and increasingly alkaline blood pH in the absence of hyperventilation. Using $TCO_2$ monitoring and ICT, an individual is instructed on how to consciously and intentionally lower his/her $TCO_2$ to minimum tolerable limits. This would also approximate the maximum tolerable alkalotic pH. This equilibrium may require several minutes depending on the preceding performance intensity. Achieving minimum $TCO_2$ values are essential in creating, or 'building', a maximum alkaline reserve. This alkaline reserve is utilized specifically to offset the anticipated surge of lactic acid caused by the upcoming obstacle. The greater the anticipated effort or difficulty, the greater the alkalosis that must be created. The athlete, therefore, is now able to actively prepare for a race or upcoming intensive effort by dropping $TCO_2$ levels to minimums established using the training methods of the instant invention.

Another novel benefit of this training system is the ability to prolong breathe-holding while performing strenuous exercise. While acidosis and hypercarbia are known potent stimulants of breathing, the opposite also holds true, i.e., the stimulus to breathe can be blunted by alkalosis and hypocarbia. If ICT is used along with $TCO_2$ biofeedback, the maximum respiratory alkalosis that can be tolerated within safe limits is established and the athlete or individual is able to safely breathe-hold for more prolonged periods of time. This technique would be invaluable and potentially life-saving to an athlete such as a kayaker or surfer who is required to breath-hold while underwater following sudden loss of control in their activity. This technique would not be appropriate for free-diving as shallow-water drowning is a well-known risk and complication under these circumstances.

A. Training Protocol

Before any training using this system is performed, baseline performance parameters are measured while the subject is using the current art, i.e., exercising using the athlete's current respiratory and ventilatory patterns. Two studies are performed: 1) Incremental Maximum Effort Test, and 2) 20-30 Minute Maximum Effort Test. Protocols for these two tests are detailed below.

Measurement of heart rate, transcutaneous $CO_2$, venous pH, and lactate can be used to illustrate comparative trends between baseline performance and performance using the training method of the instant invention. Electrolyte measurements such as venous sodium, potassium, chloride, $CO_2$ (bicarbonate), calcium, phosphate, and magnesium provide a more complete metabolic profile. These parameters will also be essential to gauge the athlete's progress and fitness level over time as well as monitor for any significant imbalances.

During instruction or performance using the present invention, one possible scenario which may lead to false and unsatisfactory results is if the subject takes rapid but sufficiently shallow breathes such that, he or she can still expire adequate amounts of $CO_2$ that accumulate passively into the lung space, but shallow enough that the alveoli will not distend to an adequate volume over which optimal oxygenation can take place. It is difficult to create a scenario where an individual can create both a hypocarbic and hypoxic environment, but it is possible to create a hypocarbic environment where oxygen reserve is reduced and ultimately insufficient for prolonged breath-holding, for while there is significant hypocarbia, and hence alkalosis, the athlete's respiratory stimulus becomes driven by hypoxia rather than hypercarbia. Inadequate respiration may create inadequate oxygen stores. While the supply of oxygen is not a variable that can be altered, and while endurance efforts are not typically associated with hypoxia, the monitoring of pulse oximetry may be particularly useful during instruction. By monitoring pulse oximetry, oxygen saturation can be kept at maximum values while the subject simultaneously maximizes $CO_2$ ventilation. Therefore, one of the goals of training is to allow an instructor to ascertain, by use of a $TCO_2$ monitor, and, in some embodiments, with a pulse oximeter, that a trainee has a sufficient balance in both the rate and depth of respiration for proper results. This phenomenon is more typically encountered and problematic when training for breath-holding during exercise.

B. Somatic Sensory Alkalosis Biofeedback Training

An integral part of the training system of the instant invention is Somatic Sensory Alkalosis Training. This step focuses on an introduction to the phenomenon of somatic sensory changes associated with the alkalotic state. $TCO_2$ monitoring is utilized as a biofeedback tool to correlate muscular sensory symptoms with increased ventilation and the associated lowering of $TCO_2$ levels. It can provide immediate feedback allowing the athlete to recognize the new somatic sensations of the alkalotic state during performance. A stationary bike is used during this author's data collection since this will minimize any artifact in $TCO_2$ monitoring associated with motion. The following methodology is used:

1) Maximum heart rate is estimated using the formula (220–age) or by using the maximum heart rate measured at the end of the Incremental Maximum Effort Test, the protocol for which is discussed below as part of "Study #1."

2) A constant cycling rpm (revolutions per minute) must be maintained. This can be achieved through a number of means including computerized methods or from a metronome.

3) The athlete is asked to warm-up and exercise at a very light level of effort, e.g. at roughly 60 to 70% of the maximum heart rate. At the chosen intensity, the trained athlete must be exercising without any element of acidosis. Baseline $TCO_2$ is established at this level of effort.

Baseline $TCO_2$ levels can be used as a valuable tool for training purposes. During an individual's routine training, baseline $TCO_2$ at this level of effort (i.e., sub-lactate threshold) is important as it may reflect recovery, or lack of, from prior exhaustive training or racing. When the athlete has not fully recovered, the muscle bed will have a reduced capacity to eliminate the muscular by-product of its metabolism, $CO_2$. As a result, baseline $TCO_2$ will be higher in the athlete who has not fully recovered from prior exhaustive racing or training. $TCO_2$ values need only rise 1 mm Hg higher than the rested state baseline $TCO_2$ for delayed recovery to be suspected. Higher elevations in baseline $TCO_2$ are associated with increasing likelihood of fatigue and delayed recovery. Fatigue may also be detected if there is either a reduction in the absolute drop in $TCO_2$ expected for a given level of intensity or if there is a reduced rate of decline in $TCO_2$ for a given rise in performance intensity.

4) The athlete is then asked to increase the intensity of exercise such that a new heart rate of approximately 75-80% of the maximum heart rate is reached. This new heart rate is maintained at a constant, stable level.

5) The athlete is then asked to increase respiration/ventilation so that $TCO_2$ is reduced by an absolute amount of approximately 5 mm Hg and down to a value no greater than 38 mm Hg. The athlete is asked to focus on the somatic changes during this transition. The lower the $TCO_2$ drops the greater the alkalotic state and hence its accompanying improvement in perceived somatic sensation.

C. Measurement of Earliest Onset of Metabolic Acidosis

The principle benefit of this training method is the elimination of acidosis at its earliest onset. The athlete must create an alkalotic state as early as possible so as to avoid any acidosis and its subsequent detrimental effects. Therefore, one must determine the earliest onset of metabolic acidosis in the exercising athlete. The onset of metabolic acidosis may be detected in the blood through various methods. For example, one can measure the earliest onset of rise in lactic acids. Another method is to measure the earliest drop below the resting baseline state in venous bicarbonate, measured as venous $CO_2$. Yet another method is via the measurement of the earliest increase in the anion gap. This is calculated using the formula of Table 4 and assumes that the individual is completely healthy:

TABLE 4

Anion Gap = [Na+] − ([Cl−] − [$CO_2$])

Using the above example, the trained athlete is instructed to start cycling at a resistance that correlates to approx. 60-70% of the maximum heart rate. Once this has been achieved, the following strategy is taken. Resistance is increased incrementally such that the heart rate is increased incrementally, no greater than 5 beats per minute per increment. At each incremental increase in heart rate, the athlete maintains this heart rate for approximately 3-5 minutes. Using a metronome ensures a constant, unchanging effort.

After 3-5 minutes at each plateau in heart rate, a venous lactate and a blood chemistry panel (sodium, potassium, chloride, and $CO_2$) is obtained. The heart rate corresponding to a rise in lactate greater than 50% of the baseline value or a rise in lactate greater than 2 mmol/L (this may be variable depending on the established norms in the assay), whichever is smaller, is used as the systemic lactate threshold. The systemic lactate threshold is differentiated from the cellular acidosis threshold as it is assumed that cellular acidosis occurs before systemic acidosis. Subtracting 5-10 beats per minute from the heart rate associated with the systemic acidosis threshold approximates the heart rate at the onset of cellular lactic acidosis. It is at this heart rate during training or racing that the athlete will require a compensatory respiratory alkalosis utilizing somatic sensory feedback. The athlete will increase ventilation at the cellular acidosis threshold so that $TCO_2$ drops approximately at least 2 mm Hg below the baseline $TCO_2$ value, although this value is a variable depending on the baseline status of the individual being tested. In the instant invention, $TCO_2$ levels should be no greater than approximately 38 mm Hg.

An embodiment of the instant invention is used to maximize the athlete's ventilatory capacity. Heart rate may be used as an indicator of intensity of effort. As resistance increases, heart rate increases. The athlete is motivated to progressively lower $TCO_2$, as heart rate and intensity increases at all times, cognizant of somatic sensory input. Through repeated practice, reproducible ideal $TCO_2$ values are correlated with heart rate values and the athlete obtains a personal profile for peak performance or motivational training purposes. In this fashion, one can maximize the benefits of training by avoiding the detrimental effects of acidosis. Periodic testing using multiple physiologic parameters is performed to follow objective performance. These include $TCO_2$, venous pH, lactate, and electrolyte panels. The ultimate goal is to perform maximal efforts without any measurable systemic acidosis.

D. $TCO_2$ and Breath-Holding

In another embodiment of the instant invention, this training system may be used to enhance the ability of the athlete to breath-hold, when appropriate, during strenuous efforts. The ability to breath-hold is proportional to the extent that $TCO_2$ is lowered for any given level of exertion.

For example, a kayaker may typically exercise at a heart rate of 85% of his or her maximum. A goal may be to train this kayaker to breath-hold for the maximum amount of time at this heart rate so that, in the event the kayak capsizes, the kayaker will feel comfortable holding his or her breath for prolonged periods of time in order to flip the boat back to the upright position. The rationale behind the training, physiologically, is twofold; 1) the kayaker can hold his or her breath longer, and 2) if the kayaker feels less urge to take in an exhaustive inspiration, anxiety will be lessened. With less anxiety there is less of an adrenergic or panic response. With less adrenaline circulating, oxygen consumption will be lower. With less oxygen consumption, there will be less $CO_2$ generated, and finally, with less $CO_2$ being generated, there will be less stimulus to breathe. As previously mentioned, reduced anxiety is present during the general state of alkalosis.

Achievement of maximal breath holding capacity requires mastery of Somatic Sensory Alkalosis Biofeedback Training according to the instant invention, including the following steps:

1) First, a target heart rate is determined. Unless already known, this is achieved through repeated continuous monitoring during performance of that sport over an adequate period of time. Using the example above, the kayaker goes out into his or her preferred watercourse that exposes the kayaker to the typical hazards and stressors he or she typically encounters. The kayaker performs his or her sport with continuous heart rate monitoring. By studying the trends associated with various efforts, a heart rate is chosen which safely approximates the typical demands of this sport. This is the heart rate at which instruction is ideally directed.

2) Using the stationary ergometer or other appropriate device, the athlete is brought through an appropriate warm-up.

3) Resistance is increased to the point where the target heart rate is reached and able to be maintained in a constant and stable pattern.

4) The athlete is then instructed to increase respiration and ventilation such that $TCO_2$ is lowered. Care must be undertaken to avoid Exertional Hyperventilation Syndrome. Exertional Hyperventilation Syndrome is likely to be more prevalent during this technique since the intent is to lower $CO_2$ levels to the lowest beneficial tolerable levels.

5) It may be more useful to acquaint the athlete to incrementally lower levels of $TCO_2$ and the associated duration of breath-holding. For example, the subject reaches the target heart rate and is then instructed to lower $TCO_2$ by 4 mm Hg. Upon reaching this new $TCO_2$ level the athlete then attempts to hold his or her breath as long as possible, while at the same time continuing to exercise maintaining the target heart rate. This process is repeated at progressively lower $TCO_2$ levels, using the same target heart rate, until the maximum duration of breath-holding is achieved.

Incidentally, breathe-holding training also represents a unique biofeedback tool since the transition to and subsequent development of acidosis following breathe-holding is achieved in seconds, allowing the individual to identify more acutely the somatic symptoms of acidosis.

What is claimed, therefore, is a method for enhanced transcutaneous carbon dioxide ($TCO_2$) control exercise training of a trainee, utilizing at least three training sessions; a primary, a secondary, and a tertiary training session. In a preferred embodiment, the secondary and tertiary training sessions are repeated as necessary to effect optimal results. Training begins with performing a first exercise training session during which the trainee is monitored with at least a cardiovascular characteristic monitor, a metabolic characteristic monitor, and a $TCO_2$ monitor. During this primary session, the $TCO_2$ of the trainee at rest is recorded, thereby establishing a first baseline $TCO_2$ value. Exercise of the trainee is initiated at progressively increasing intensity, while allowing the trainee to view the $TCO_2$ monitor. Then, (i) at least one primary cardiovascular characteristic value reflecting exercise intensity, (ii) at least one primary metabolic characteristic value reflecting blood acid-base balance, and (iii) at least one $TCO_2$ value; are monitored and recorded at least at a first and a second time.

The exercise intensity of the trainee is progressively increased, as measured by the primary cardiovascular characteristic value, to a point of maximum effort, and a measured maximum effort cardiovascular characteristic value reflecting the primary cardiovascular characteristic value at the point of maximum effort is both monitored and recorded.

A maximum cardiovascular characteristic value reflecting exercise intensity is then determined, selected from one of the group of values consisting of (i) an age determined formula based maximum heart rate value for the trainee and (ii) the recorded measured maximum effort cardiovascular characteristic value. A correlation is then made between the at least one primary cardiovascular characteristic value and the at least one metabolic characteristic value for each of the at least first and second times.

Next, a lactate threshold (LT) value selected from a group of values consisting of the at least one primary metabolic characteristic value is determined, by reference to a predetermined reference criteria and then a determination is made of the recorded primary cardiovascular characteristic value at the LT value.

A target cardiovascular characteristic value is calculated, less by a predetermined measure, than the recorded primary cardiovascular characteristic value at the lactate threshold (LT) value; and then the trainee is rested for a time sufficient to attain a training baseline $TCO_2$ value not greater than 110% of the first baseline $TCO_2$.

In at least one secondary exercise training session, which the trainee is monitored with at least a cardiovascular characteristic monitor and a $TCO_2$ monitor, and performs the following steps. Exercise of the trainee is initiated at progressively increasing intensity, as measured by the primary cardiovascular characteristic value and monitoring and recording $TCO_2$ values while the trainee is allowed to view the $TCO_2$ monitor, to a steady state exercise intensity at which the trainee attains the target cardiovascular characteristic value.

Next, the trainee identifies a sensed somatic state by instructing the trainee to increase ventilation to reduce the monitored and recorded $TCO_2$ values to an at least one predetermined $TCO_2$ value, while instructing the trainee to identify and correlate at least one physiologic sensation with the at least one predetermined $TCO_2$ value. The trainee is then rested for a time sufficient to attain the training baseline $TCO_2$ value; and the secondary exercise training session may be repeated until the trainee is able to identify the sensed somatic state without viewing the $TCO_2$ monitor. Training success is monitored by verifying that the identification of the sensed somatic state by the trainee correlates to within a first predetermined range above and below the at least one predetermined $TCO_2$ value. The secondary exercise training sessions end by resting the trainee for a time sufficient to attain the training baseline $TCO_2$ value.

In at least one tertiary exercise training session, the trainee is monitored with at least a cardiovascular characteristic monitor and a $TCO_2$ monitor, and performs the following steps. Exercise of the trainee is initiated at progressively increasing intensity as measured by the primary cardiovascular characteristic value, while not allowing the trainee to view the $TCO_2$ monitor. The primary cardiovascular characteristic value is monitored while continuing to progressively increase the exercise intensity of the trainee to a point at which the trainee attains the target cardiovascular characteristic value. The trainee is then instructed to adjust ventilation to achieve an at least one predetermined $TCO_2$ value based on the perception of the sensed somatic state. Training success is monitored by verifying that the trainee has adjusted ventilation so as to attain at least one of the predetermined $TCO_2$ values within a second predetermined range above and below the at least one predetermined $TCO_2$ value.

In embodiments of the method, the cardiovascular characteristic monitor may further include at least a heart rate monitor and may further include at least a pulse oximeter. The metabolic characteristic monitor may further include at least one laboratory measurement value derived from a laboratory measurement performed on a quantity of venous blood drawn from an indwelling venous catheter. Alternatively, finger stick capillary blood may be utilized for testing. The at least one laboratory measurement value may include at least one laboratory measurement value selected from a group of consisting of measurement of venous or capillary lactate, venous $CO_2$, pH, and bicarbonate ($HCO_3^-$) values.

The method may also include exercise at progressively increasing intensity that further includes at least a first level and a second level of exercise intensity performed at a predetermined exercise intensity for a predetermined period of time.

In embodiments of the method, the at least one primary cardiovascular characteristic value reflecting exercise intensity may be heart rate, and the at least one primary metabolic characteristic value reflecting acid base balance may be an acid base balance value selected from the group of laboratory measurement values selected from the group consisting of venous lactate, venous CO2, venous pH, and venous bicarbonate ($HCO_3^-$) values.

The age determined formula based maximum heart rate value may be calculated by subtracting an age of the trainee in years from 220. The predetermined measurement criteria determining the LT value may be further determined as a first occurring in time venous lactate value having a value greater than 2.0 mmol/l during exercise of progressively increasing intensity or, in a preferred embodiment, as a first occurring in time primary metabolic characteristic value selected from the group of values reflecting a rise in value of at least 50% over baseline values and a value of blood lactate greater than 2.0 mmol/l, and a laboratory lactate level greater than the standardized normal values for the assay, during exercise of progressively increasing intensity.

Figure 15:
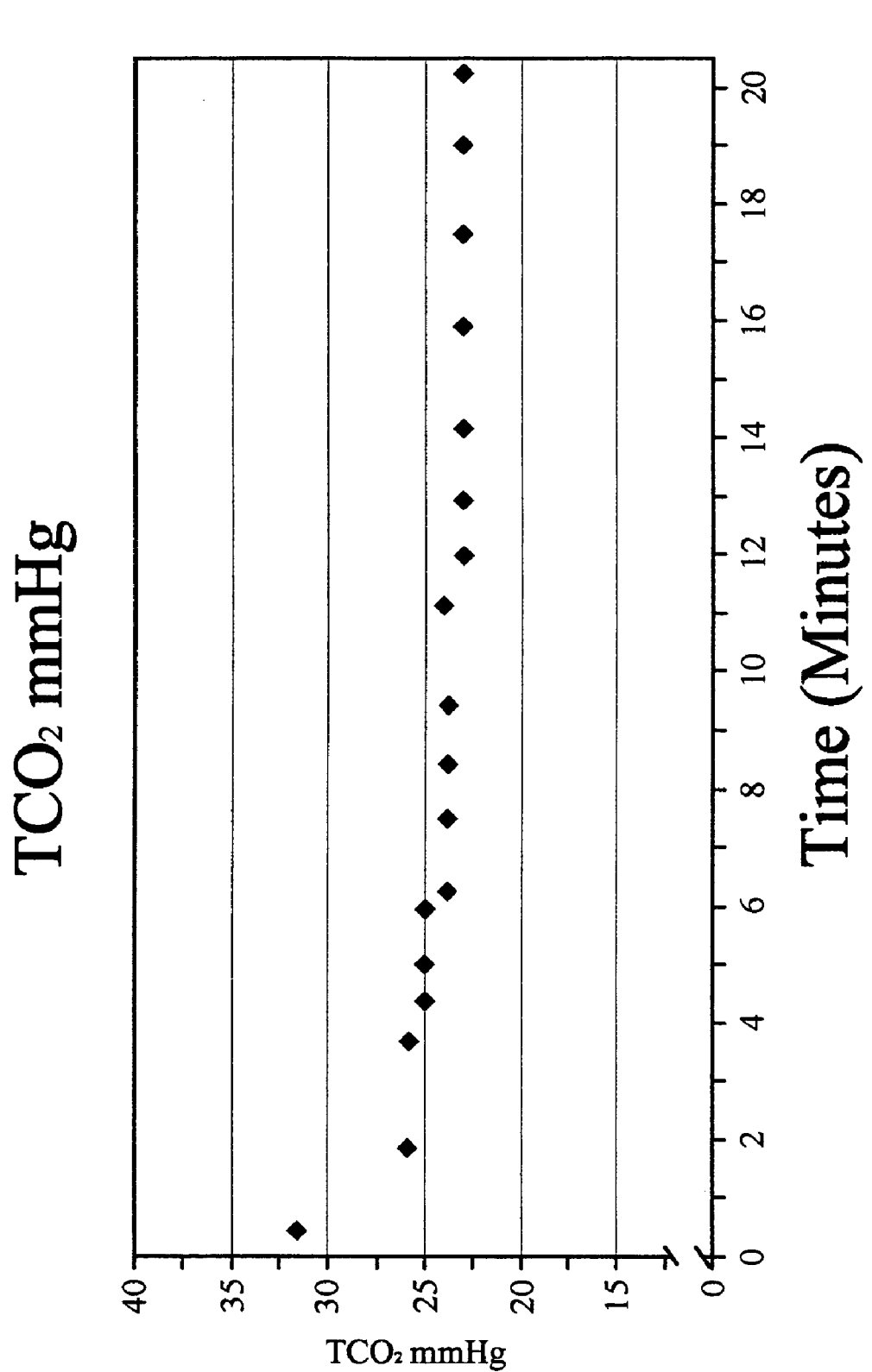
FIG. 15 shows $TCO_2$ as a function of time in an experimental subject in an embodiment of the instant invention.

The calculation of the target cardiovascular characteristic value may be equal to or more than 0.80 of the primary cardiovascular value at the LT value. The at least one predetermined $TCO_2$ value may be equal to or more than 70% of the first baseline $TCO_2$ value. The first predetermined range above and below the at least one predetermined $TCO_2$ value may be a range of less than or equal to 5 mmHg above and below the at least one predetermined $TCO_2$ value and the second predetermined range above and below the at least one predetermined $TCO_2$ value may be a range of less than or equal to 5 mmHg above and below the at least one predetermined $TCO_2$ value. While $TCO_2$ values may be decreased by more than 50% (See FIG. 15), such intense lowering may not be compatible with maximal performance.

In another embodiment, the instant invention supplied a controlled breathing method for increasing an alkaline reserve of an individual. The method includes the steps of measuring a baseline respiratory status characteristic value prior to exercise and then exercising in a progressively graded manner. Before and during exercise; at least one acid-base characteristic value; at least one exercising respiratory status characteristic value; and at least one cardiovascular characteristic are all measured and recorded.

An LT respiratory characteristic value is determined representing the at least one respiratory status characteristic and an LT cardiovascular characteristic value is determined representing the cardiovascular characteristic value at a point at which measurement of the acid-base characteristic value indicates a non-linear accumulation of lactic acid.

A target cardiovascular characteristic value is determined that is less than the LT cardiovascular characteristic value by a predetermined amount, and the trainee increases ventilation at a level of exercise intensity producing the target cardiovascular characteristic value, to achieve a training respiratory characteristic value that is less than the baseline respiratory status characteristic value.

In yet another embodiment of the method, a method includes a breathing technique for increasing the alkaline reserve of an individual, including the following steps. Firstly, a respiratory excretion level of carbon dioxide by the individual during ventilation is monitored. Next, ventilation is increased to increase the respiratory excretion level of carbon dioxide, while the respiratory excretion level of carbon dioxide concurrent with increased ventilation is monitored. Lastly, ventilation is modulated to produce a predetermined target respiratory excretion level of carbon dioxide as indicated by the monitored respiratory excretion level.

In this, as well as other, embodiments, the steps of monitoring a respiratory excretion level of carbon dioxide further may further include the step of monitoring at least one $TCO_2$ level.

In yet another embodiment, the method includes a technique for teaching controlled breathing for maximizing breath holding time of an individual, including the following steps. At least one normal exercise heart rate value as measured during predetermined exercise is determined and then the trainee is rested for a predetermined time. While monitoring at least one $TCO_2$ level, exercising is intensified sufficiently to produce the normal exercise heart rate and ventilation is increased sufficiently to lower the at least one $TCO_2$ level to a predetermined $TCO_2$ level;

The trainee then suspends ventilation for a maximum amount of time physiologically possible while maintaining exercise at the intensity sufficient to produce the normal exercise heart rate. The steps of this embodiment may then be repeated, decreasing with each repetition the predetermined $TCO_2$ level achieved by increasing ventilation, until a point is reached at which additional decreases in the predetermined $TCO_2$ level achieved by increasing ventilation do not increase the time possible to suspend ventilation for the maximum amount of time physiologically possible while maintaining exercise at the intensity sufficient to produce the normal exercise heart rate.

Studies

Two studies were performed to demonstrate the benefit of training using $TCO_2$ monitoring. Two healthy male subjects (Athlete A—age 43, and Athlete B—age 37) with extensive athletic experience and training using this technique. Both athletes performed the first phase of study in the same test session. The most experienced athlete with this training method (Athlete A) performed the second phase of study.

Both studies were undertaken at similar times and identical locations. Prior to starting each test, a heparin lock catheter was inserted into the antecubital vein through which venous blood samples were collected. All blood specimens were measured using standardized hospital analysis equipment.

The heart rate was continuously monitored during testing. A transcutaneous $CO_2$ monitor was attached to the middle aspect of the deltoid muscle, considered one of the optimum areas for $TCO_2$ monitoring. Response time ($t_{90}$) for transcutaneous measurements of $CO_2$ is calibrated at 45 seconds. The electrodes were heated to 45 degrees Celsius, as this slightly elevated temperature is associated with improved accuracy in measurement of gas exchange parameters. Estimation of gas exchange parameters using $TCO_2$ monitoring during exercise testing has been validated provided the electrode is heated to 45 degrees Celsius and the work load increments are gradual, allowing for the latency in the response time of the system.

Study #1: Incremental Maximum Effort Test

The object of this test was to estimate maximum heart rate, maximum intensity of effort levels and the associated biochemical parameters. During this phase of testing, both athletes were not allowed to view the $TCO_2$ monitor. Being blinded to the $TCO_2$ monitor allowed a demonstration of how an athlete can use somatic signals of acidosis to adjust ventilation in order to create an early and enhanced respiratory alkalosis. Not only should an early alkalosis be created around the lactate threshold, there should also be an absence of any acidosis, through the spectrum of intensity up to and including maximum effort. Test parameters included heart rate (heart rate), $TCO_2$, and venous blood sampling of lactate, pH, and $CO_2$ (bicarbonate). Recently, it has been shown that venous pH estimation shows a high degree of correlation and agreement with the arterial value, with acceptably narrow (95%) limits of agreement. Venous $CO_2$ is considered an indirect measure of bicarbonate, the major buffering agent in the blood other than hemoglobin. Venous $CO_2$ can be a more accurate measurement of true blood bicarbonate, as arterial bicarbonate levels are calculated, rather than measured, using other arterial blood gas indices. Venous $CO_2$ is not equivalent to arterial $CO_2$, the latter of which is measured via $TCO_2$ monitoring. Venous pH, bicarbonate and $TCO_2$ give a useful acid/base picture in the exercising athlete.

Following an ample warm-up, testing was initiated at a heart rate known to be well below each athlete's lactate threshold. At this point, one and a half minute intervals were performed at incrementally increasing workloads. At the end of each interval, heart rate and $TCO_2$ were recorded, and venous blood drawn for the measurement of $CO_2$, lactate, and pH.

A spinner was utilized where resistance was manually and incrementally increased every one and one half minutes. Using a metronome, Athlete A performed the test spinning at 108 revolutions per minute (rpm) and Athlete B at 92 rpm. The final venous blood draw was taken at the time of exhaustion. Exhaustion was defined as that point in time when the athlete was unable to maintain the established rpm with progressively increasing resistance at the established one and one half minute intervals.

Study #2: 20 Minute Maximum Effort Test

This test was performed approximately one month following the Incremental Maximum Effort Test. There were two significant changes in protocol. In contrast to the Incremental Maximum Effort Test, resistance was increased prior to onset of testing, following ample warm-up, to a level where the maximum heart rate (180) was reached. In addition to this requirement, the athlete was allowed to view $TCO_2$ levels, i.e., the athlete was not blinded to $TCO_2$ levels. By being able to view $TCO_2$ values, the athlete is able to view motivational biofeedback to create a maximum and quantifiable alkaline reserve. The goal is to create and maintain the lowest $TCO_2$ level during this maximal effort without developing signs and symptoms of acidosis or hyperventilation syndrome.

When these criteria were met, the testing was initiated. In this arm of testing, resistance remained unchanged for a 20-minute duration. The athlete performed the test while cycling at a rate of 108 rpm. The final recording and venous blood draw was taken at the 20 minute mark. Heart rate and $TCO_2$ were monitored continuously. Venous blood was withdrawn at regular one and one half minute intervals. Baseline $TCO_2$ was 40 prior to initiation of the warm-up.

Venous blood testing was expanded to include not only $CO_2$, lactate and pH, but also potassium and calcium, as these are important electrolytes that can become acutely altered with the metabolic state of acidosis or alkalosis. Alkalotic states may induce hypokalemia and hypocalcemia, respectively. The calcium level measured is representative of the total serum calcium, as opposed to the ionized form.

Results

Study # 1: Incremental Maximum Effort Test

Figure 7:
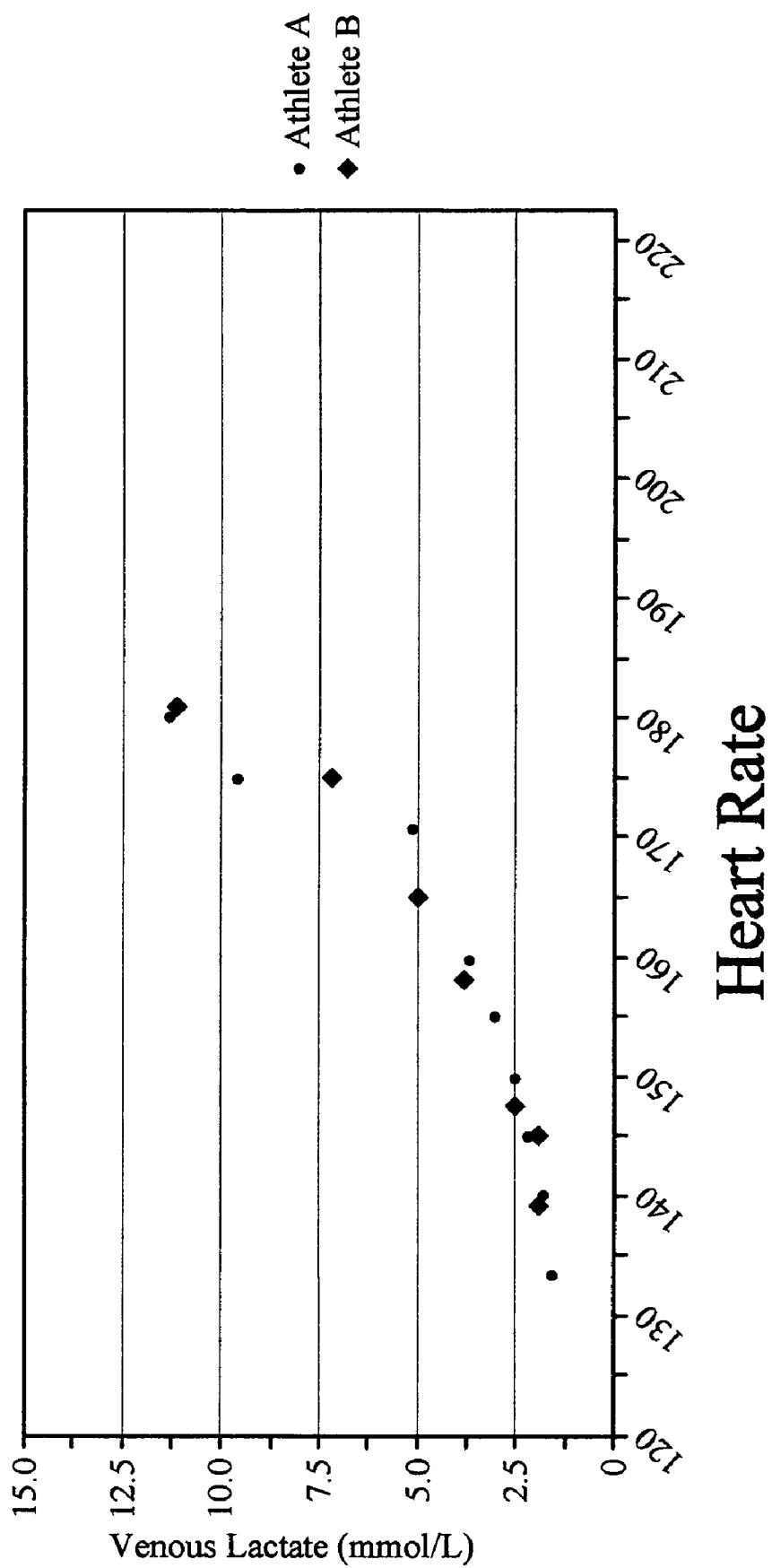
FIG. 7 shows values of venous lactate as a function of heart rate in two experimental subjects in one embodiment of the instant invention.

Results of venous lactate determinations gathered were plotted against heart rate, as seen in FIG. 7. Heart rate is considered an indicator of intensity. In the Incremental Maximum Effort test a maximum heart rate of 180 was accomplished for Athlete A and 181 for Athlete B. Venous lactate values rose to a maximum of 11.3 and 11.1 for Athlete A and B respectively. Lactate levels initially rose in a linear fashion but then became noticeably steeper after reaching levels of 5.1 at a heart rate of 171 for Athlete A and 7.2 at a heart rate of 176 for Athletes.

The term lactate threshold may be defined, as it is by McCardle, as the highest oxygen consumption or exercise intensity with less than a 1.0 mmol/L increase in blood lactate concentration above the pre-exercise level. This often correlates with a value of approximately 2.5 mmol/L.

Figure 8:
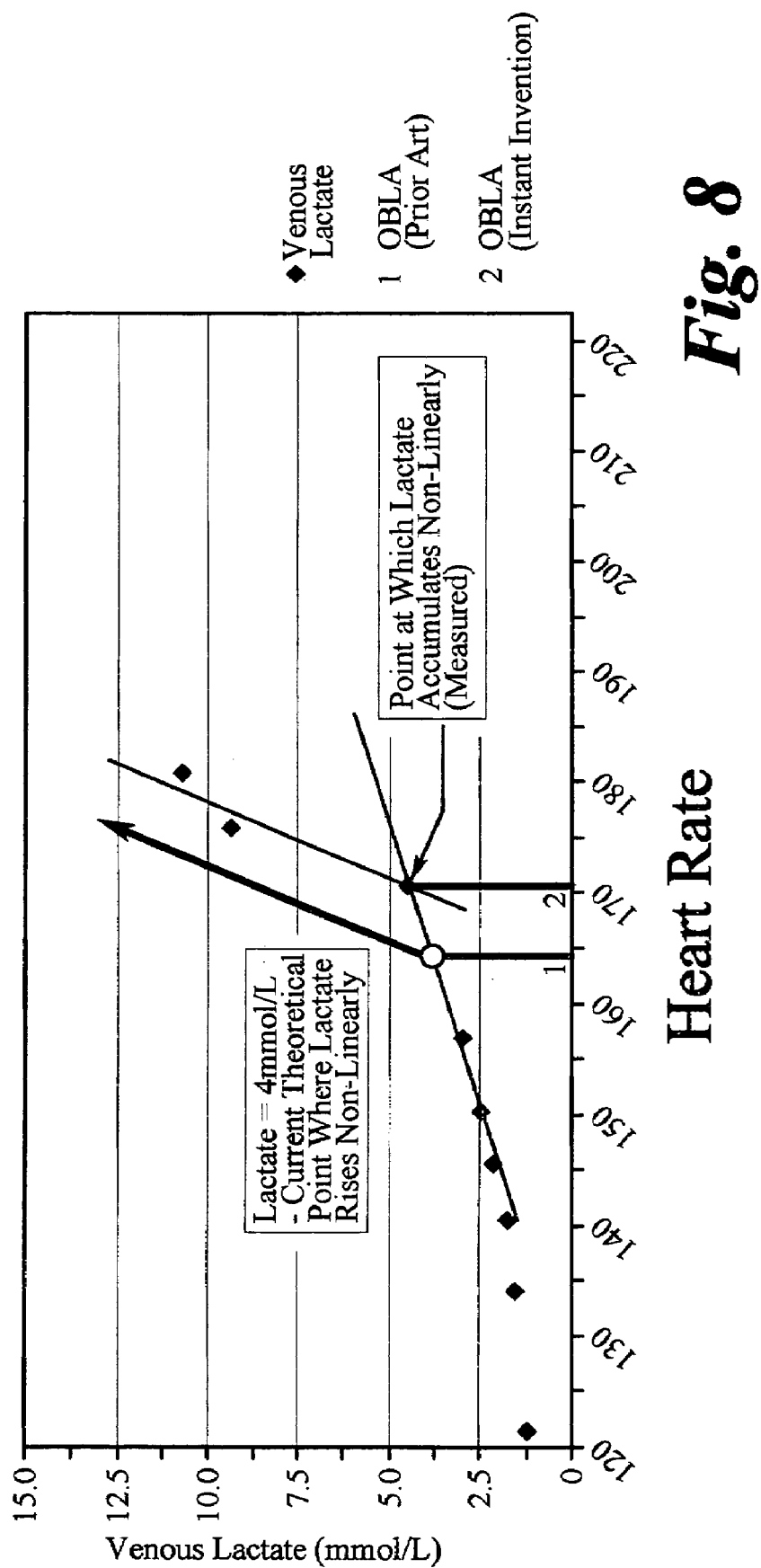
FIG. 8 shows values of venous lactate as a function of heart rate in an experimental subject in one embodiment of the instant invention, illustrating PMA values as predicted by the current art, as well as PMA values observed in the instant invention.

A 1.0 mmol/L increase (using a baseline lactate of 1.2 mmol/L as obtained only in Athlete A and seen in FIG. 7) occurred approximately at a heart rate of 145 in Athlete A. This heart rate represents approximately 80% of the maximum heart rate for this athlete. As seen in FIG. 8, if the lactate threshold is defined as the heart rate where lactate is 2.5 mmol/L, the lactate thresholds for Athlete A and B would be 150 and 147 respectively, corresponding to 83 and 81% of the maximum heart rate for these athletes. All these values fall between narrow limits and the lactate threshold can be considered in the two subject athletes to fall between approximately 80% to 83% of the maximum heart rate. It is, however, probable that lactic acidosis at the cellular level occurs earlier than that which is measurable in the systemic circulation.

Athlete A's lactate levels, seen in FIG. 8, do not rise exponentially at 4 mmol/L using the training methods of the instant invention because the athlete is actively maintaining an alkalotic state, even beyond the 4 mmol/L concentration level. The result is an ongoing rise in lactate but in a linear rather than exponentially increasing fashion. Using prior art training methods, the point of metabolic acidosis, or PMA, signals the beginning of an exponential rise in lactate because performance continues in an acidotic state.

Using the definition of OBLA as that of a lactate level of approximately 4 mmol/L, OBLA correlated with an approximate heart rate of 163 beats per minute for Athlete A and 156 for Athlete B. These correspond to 91% and 86% respectively of the maximum heart rate values. The onset of OBLA at 91 and 86% of maximum heart rate is, in itself, remarkable considering that the athletes tested would not be considered elite athletes.

Figure 9:
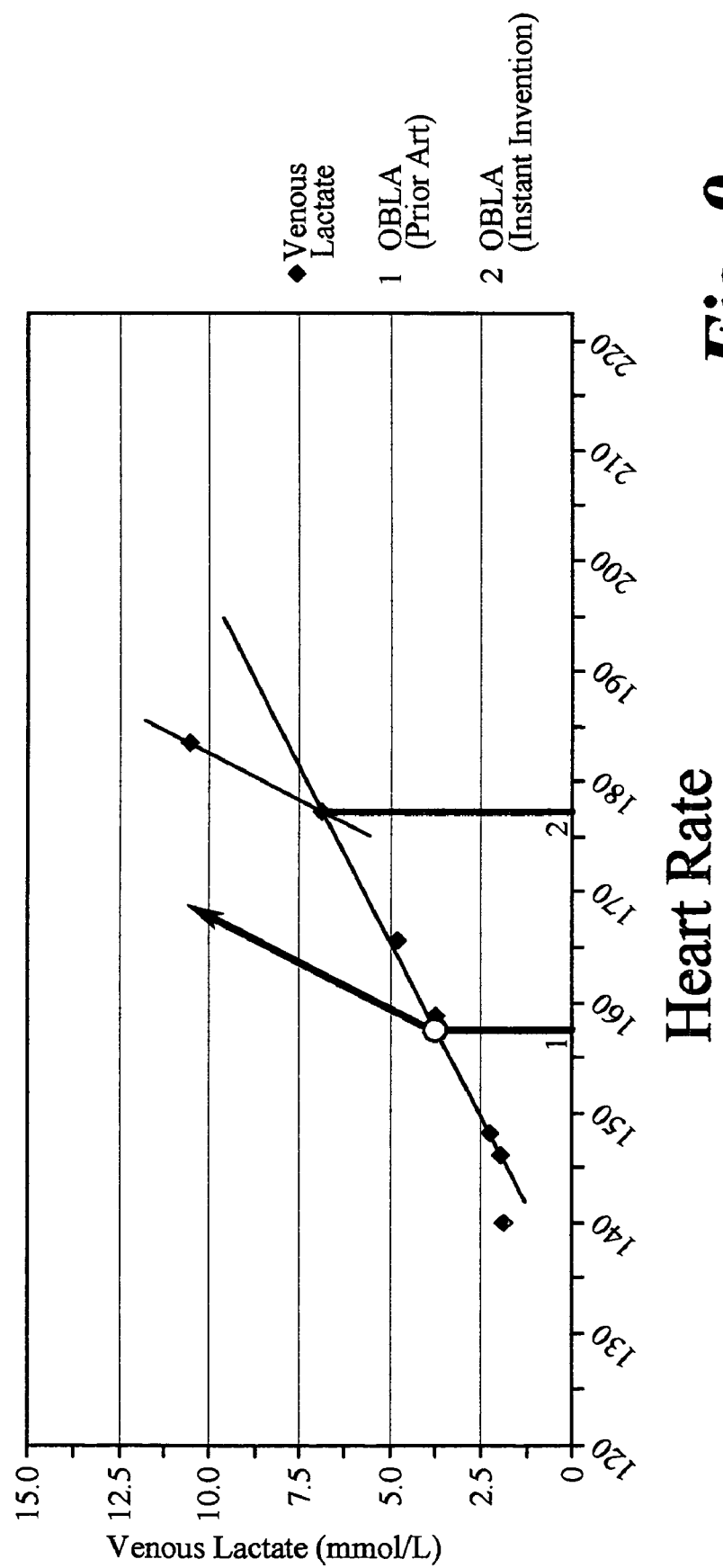
FIG. 9 shows values of venous lactate as a function of heart rate in another experimental subject in one embodiment of the instant invention, illustrating PMA values as predicted by the current art, as well as PMA values observed in the instant invention.

Using a more general definition of OBLA, i.e., the heart rate at which lactate levels rise measurably steeper or exponentially, OBLA was correlated using the instant invention with a lactate of 5 and 7 mmol/L and an approximate heart rate of 171 and 176 for Athlete A and B respectively (FIGS. 8 and 9). These heart rates represent 95% and 97% of the maximum heart rate. OBLA, or rather, the maximum intensity of effort that can be sustained, has been dramatically raised demonstrating a clear improvement in performance efficiency and improvement utilizing the instant invention.

The difference in lactate values between OBLA as defined by McCardle and that of the instant invention allows a 25 and 75% increase before lactate rises exponentially using the instant invention. The difference in heart rate between OBLA as defined by McCardle and the instant invention is 8 and 20 beats per minute. This represents an allowable increase in heart rate of 4.4 and 11% for Athlete A and B respectively before lactate concentrations rise exponentially.

Figure 10:
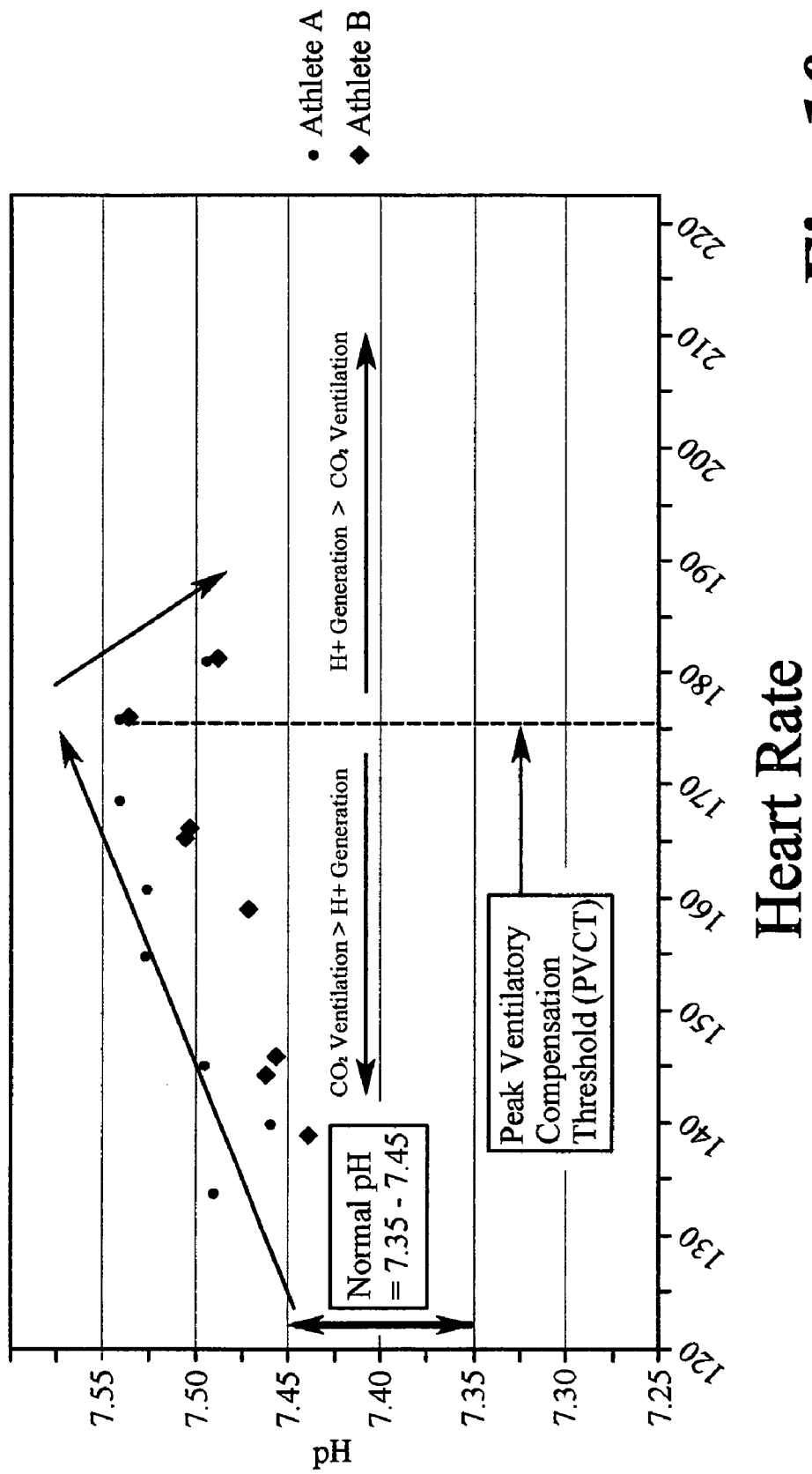
FIG. 10 shows venous pH as a function of heart rate in two experimental subjects in an embodiment of the instant invention.

Venous pH values, seen in FIG. 10, trended in a pyramidal pattern with a rise occurring around the lactate threshold (heart rate 145 for both Athletes A and B), and then a steep drop after heart rates of 175 and 176 for Athlete A and B, respectively. Only a single pH was measured in the neutral range and this was at a lighter effort. All other pH's were in the alkaline range. The point at which venous pH drops steeply prior to exhaustion is the Peak Ventilatory Compensation Threshold (PVCT). It is the point at which the athlete is unable to match $H^+$ generation with $CO_2$ ventilation. At this point the direction of the equation of Table 3 is shifted to the left with hydrogen ions now spilling over, unable to be matched by $CO_2$ ventilation. The pH is still alkalotic but there is a definite trend for a declining pH, a sign of imminent failure. Venous pH at exhaustion was 7.489 and 7.471 for Athlete A and B.

Measurements of pH in this range are still considered to be alkaline, i.e., an alkaline pH is measured at the point of exhaustion. With this alkalotic pH at exhaustion, it is important to note that with the instant invention, acidosis does not represent the limiting factor in this maximum effort test. At the point of exhaustion, the athlete is at his/her ventilatory limit. Any attempt to increase or maintain intensity will be met with a precipitous increase in acidosis and near instantaneous performance failure. This titration of ventilation against rise in lactic acid/$CO_2$ is indeed precarious and represents the true limits of performance, i.e., where the individual has truly exhausted his or her exertional respiratory reserve and achieved maximum voluntary ventilation during exercise.

Figure 11:
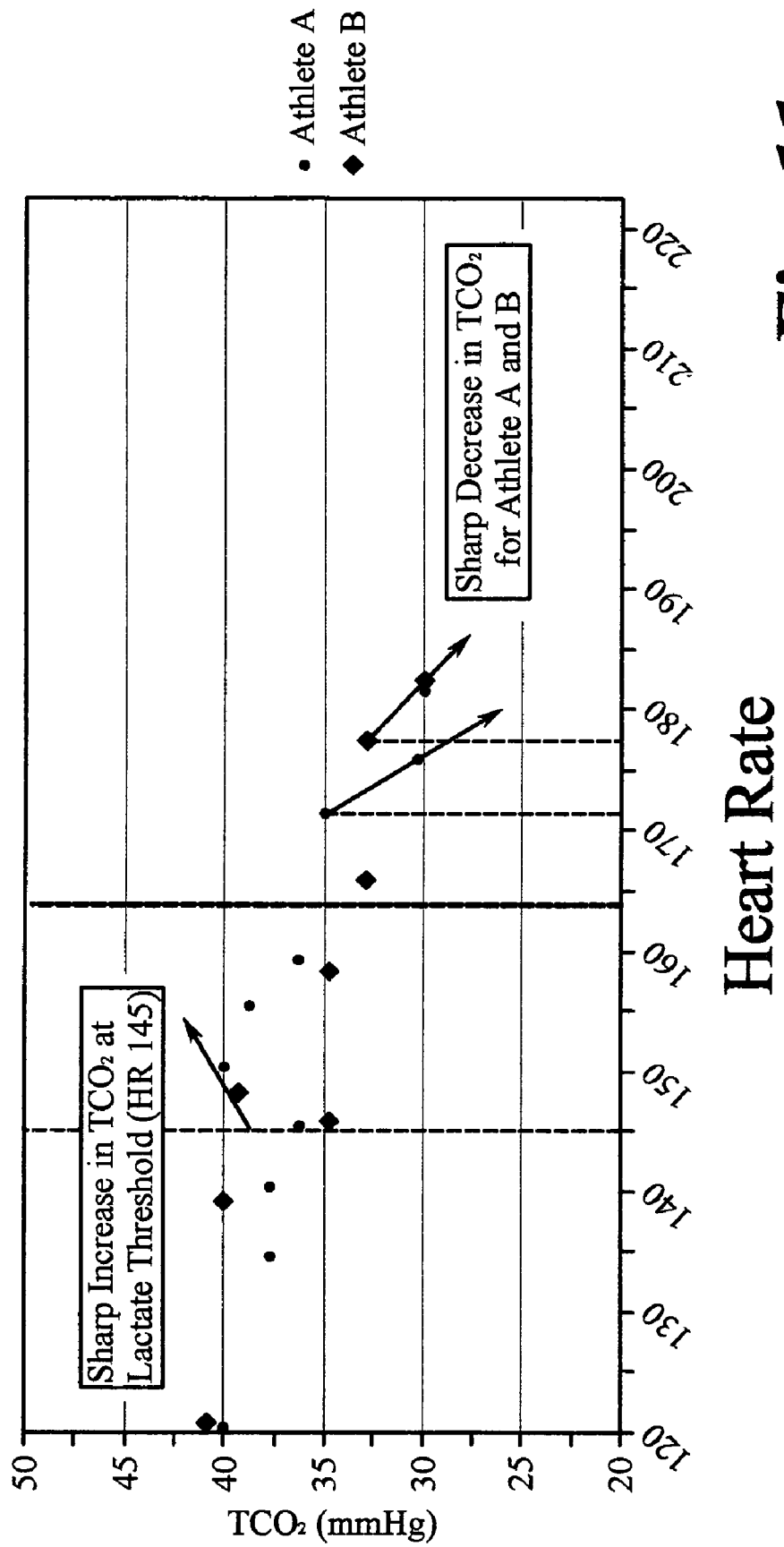
FIG. 11 shows $TCO_2$ as a function of heart rate in two experimental subjects in an embodiment of the instant invention.

Baseline $TCO_2$ started in the middle range of normal values, approximately 40 mm Hg for both athletes, as seen in FIG. 11. After the onset of testing, $TCO_2$ trended to decrease immediately, even prior to the lactate threshold. At a heart rate of 145 for both Athletes A and B, $TCO_2$ rose slightly but noticeably, although not above baseline values. This corresponds roughly to the generation of non-metabolic $CO_2$, or ventilatory threshold, where $CO_2$ rises as lactic acid initially appears and is buffered by $HCO_3^-$. $TCO_2$ levels drop thereafter as the athlete detects the acidosis and reacts by actively ventilating and lowering arterial $CO_2$. $TCO_2$ levels drop sharply at heart rates of approximately 171 and 176 for Athlete A and B respectively. This point represents a shift in balance and correlates with the Peak Ventilatory Compensation Threshold (PVCT). This corresponds to the point where ventilation is not matching the ongoing rise in $H^+$ and the shift is towards decreasing alkalosis or increasing acidosis. Lactic acid continues to rise as it is being generated by exercising muscle exposed to increasing intensity. Nevertheless, a sufficient buffering alkaline reserve has been created and there is still an opportunity for the athlete to increase the level of intensity, still efficiently. Any further elevation of lactic acid is buffered by this alkaline reserve.

Following this PVCT, $TCO_2$ values once again continue to show a progressive decline reaching identical minimum values, 30, for both athletes at exhaustion. This corresponds to 75% of baseline $TCO_2$ (baseline $TCO_2$ of 40 with drop to minimum of 30). $TCO_2$ did not rise above baseline values throughout the duration of testing, indicating a persistent over-compensation of ventilation. Over-compensating ventilation will result in a respiratory alkalosis.

Figure 12:
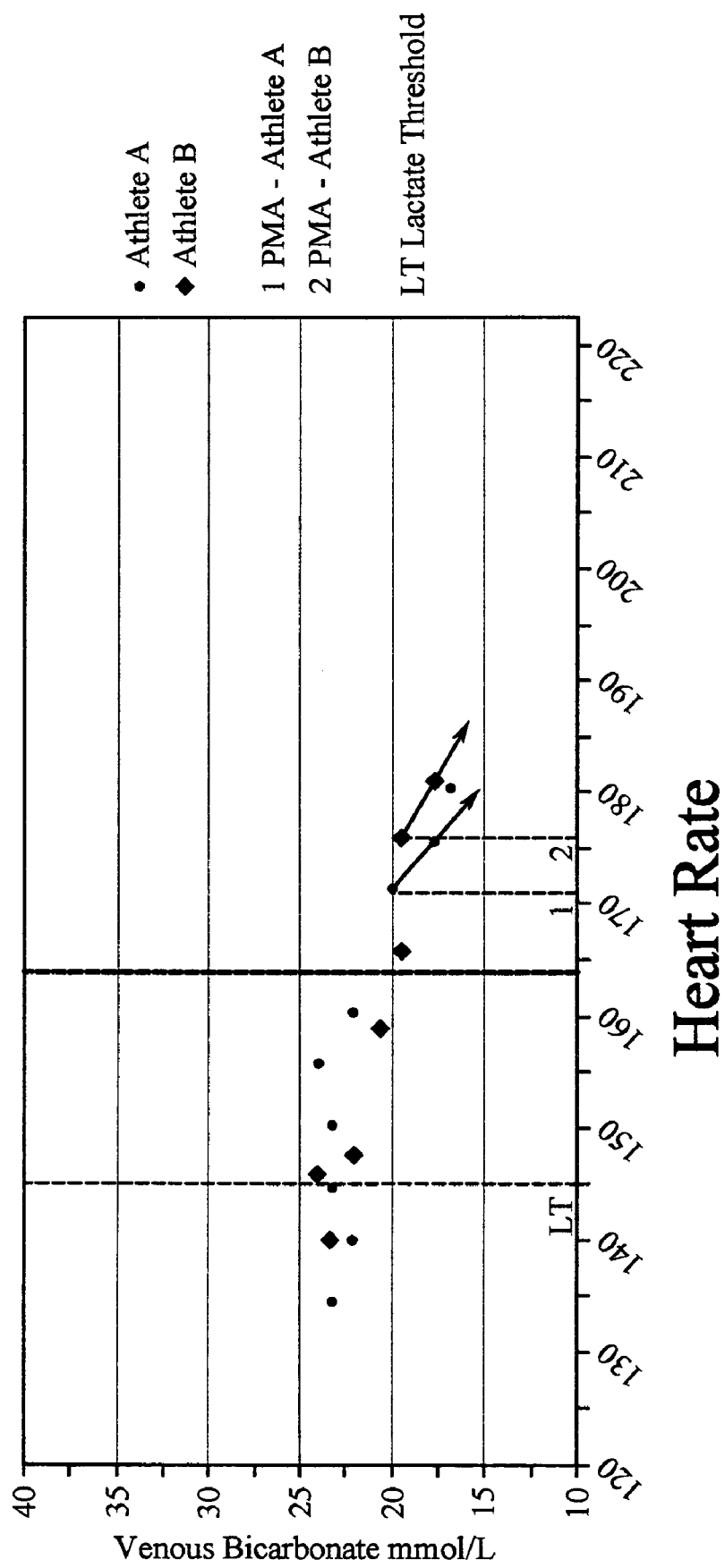
FIG. 12 shows venous bicarbonate ($CO_2$) as a function of heart rate in two experimental subjects in an embodiment of the instant invention.

Venous bicarbonate ($HCO_3^-$ values for both Athletes A and B started in the low normal range, seen in FIG. 12, with the trend correlating roughly with $TCO_2$ trends (FIG. 11). While $TCO_2$ is indicative of ventilation, bicarbonate ($HCO_3^-$) is more indicative of a metabolic acidosis, whereby acid is neutralized by bicarbonate. Minimum $HCO_3^-$ values converged on similar minimum values at exhaustion, 16 and 17 mmol/L, for both athletes. Using a baseline value of 26 (normal range=22-30 mmol/L), these values represent a drop of 38% and 35% respectively. Precipitous drops in venous bicarbonate occurred at heart rates of 171 for Athlete A and 176 for Athlete B. These heart rates again approximate the PVCT. These heart rates represent 95 and 97% of the maximum heart rate.

Study #2: 20 Minute Maximum Effort Test

Figure 13:
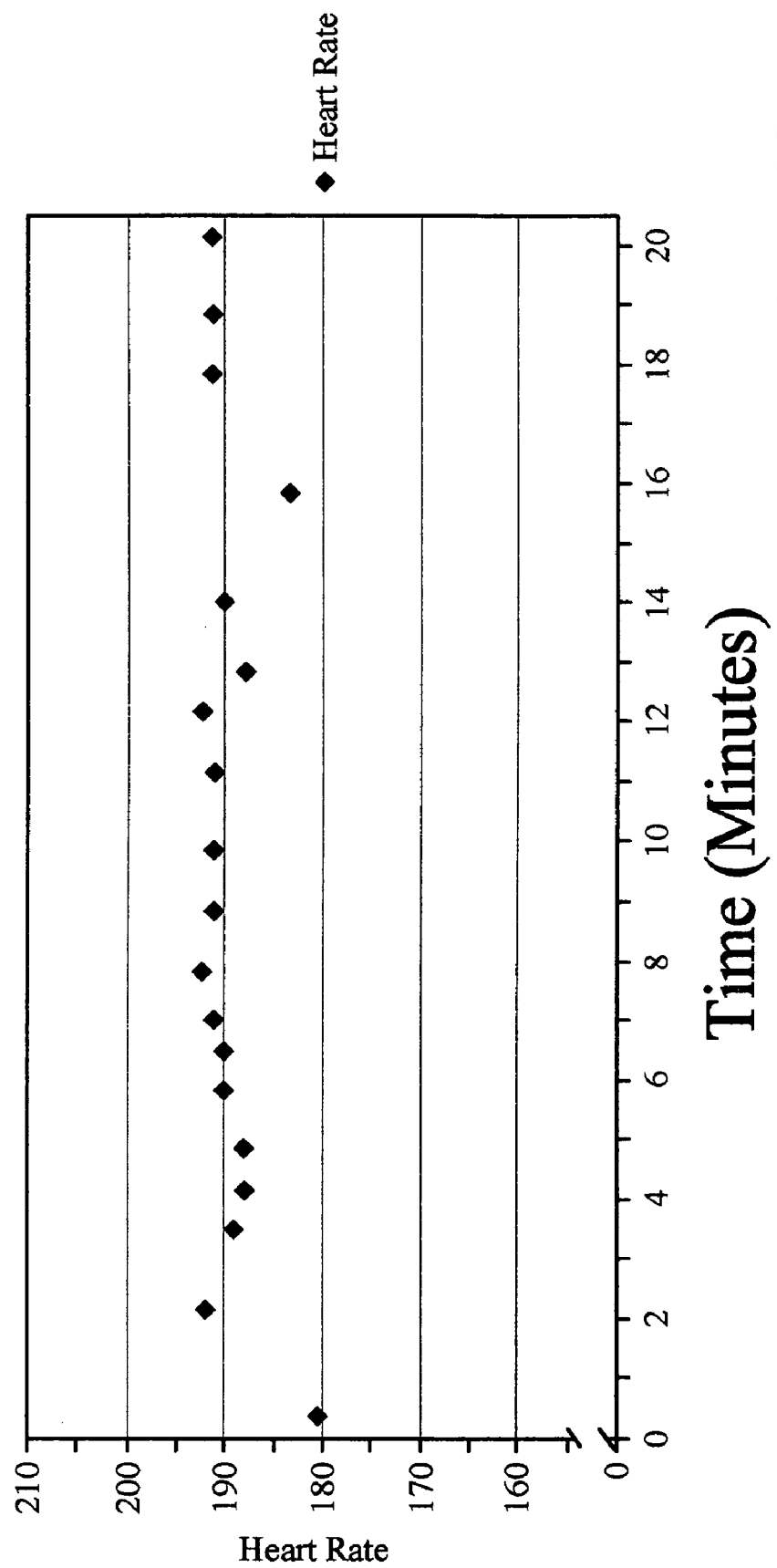
FIG. 13 shows heart rate as a function of time under exercise in an experimental subject in an embodiment of the instant invention.

Heart rate during the 20 minute maximum effort test, seen in FIG. 13, remained relatively constant at approximately 191 beats per minute. This value was 10 beats per minute, or 5%, greater than the maximum heart rate measured during the Incremental Maximum Effort Test.

Figure 14:
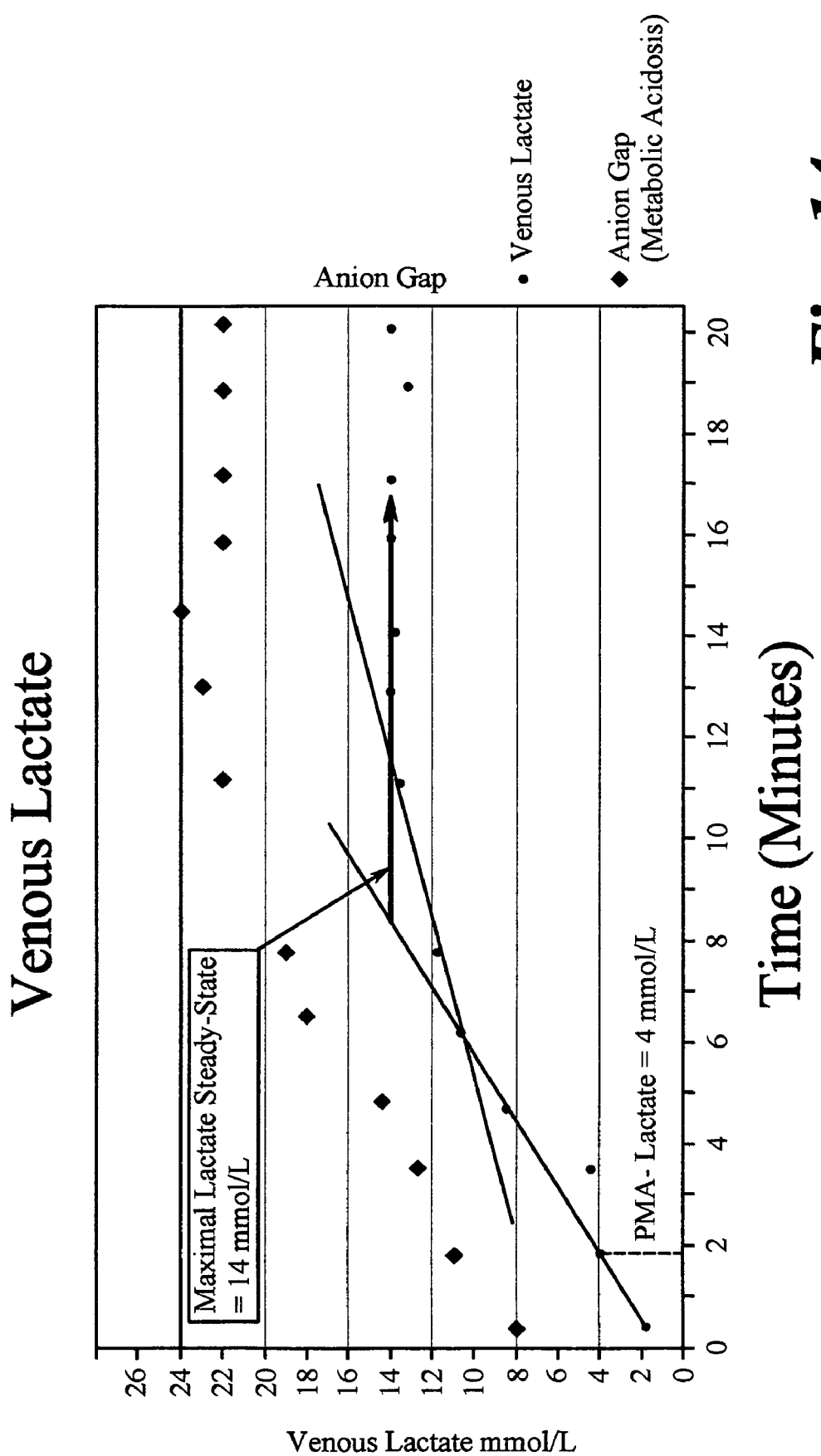
FIG. 14 shows venous lactate and anion gap as a function of time in an experimental subject in an embodiment of the instant invention.

Venous lactate, seen in FIG. 14, rose in a linear fashion and then tapered to an average maximum lactate value of approximately 14 mmol/L, where it remained for the duration of the test. Lactate levels did not reach this maximum until approximately 12 minutes of maximum effort. At this point a lactate steady state is achieved. This level is termed the maximal lactate steady state (MLSS). The maximal lactate steady state is defined as the highest blood lactate concentration and workload that can be maintained over time without a continual blood lactate accumulation. A close relationship between endurance sport performance and MLSS has been reported. MLSS has been reported to demonstrate a great variability between individuals (from 2-8 mmol/L) in capillary blood and is not believed to be related to workload. Trained endurance athletes can sustain steady-rate exercise at intensities between 80 and 90% of their maximum capacity.

Note, as seen in FIG. 14, that there is no exponential rise in lactate after a lactate concentration of 4-7 mmol/L is reached. There is a linear rise in lactate to 11 mmol/L over 6 minutes, followed by a decline in the rate of accumulation over the next 6 minutes, followed by a plateau at a MLSS of 14 mmol/L, an extreme level well above that reported in the prior art. It has been shown that there is an age-related decline in MLSS, and therefore, a 14 mmol/L MLSS in 43 year old athlete is a dramatic testament to the buffering reserve that $TCO_2$ monitoring and biofeedback of the instant invention can provide.

The anion gap is a significant tool used in evaluation acid-base disorders. With rare exceptions, an elevated anion gap is indicative of metabolic acidosis. As seen in FIG. 14, the anion gap rises, i.e., a metabolic acidosis is measured from the start of exercise testing when the lactate level starts at 2 mmol/L. A pure metabolic acidosis results in an equal fall in $HCO_3^-$. Any deviation from this relationship should be viewed as a mixed acid-base disorder. Indeed, as observed in FIG. 14, the anion gap increases by 14, which one would expect with the elevation in lactate of 14, from 8 to 22, with a fall in $HCO_3^-$ of 10, from 24 to 14. This discrepancy, as one would expect an equal fall in $HCO_3^-$ of 14 from 24 to 10 in a pure metabolic acidosis, therefore represents a mixed acid/base disorder known to be a metabolic acidosis with compensatory respiratory alkalosis.

Figure 16:
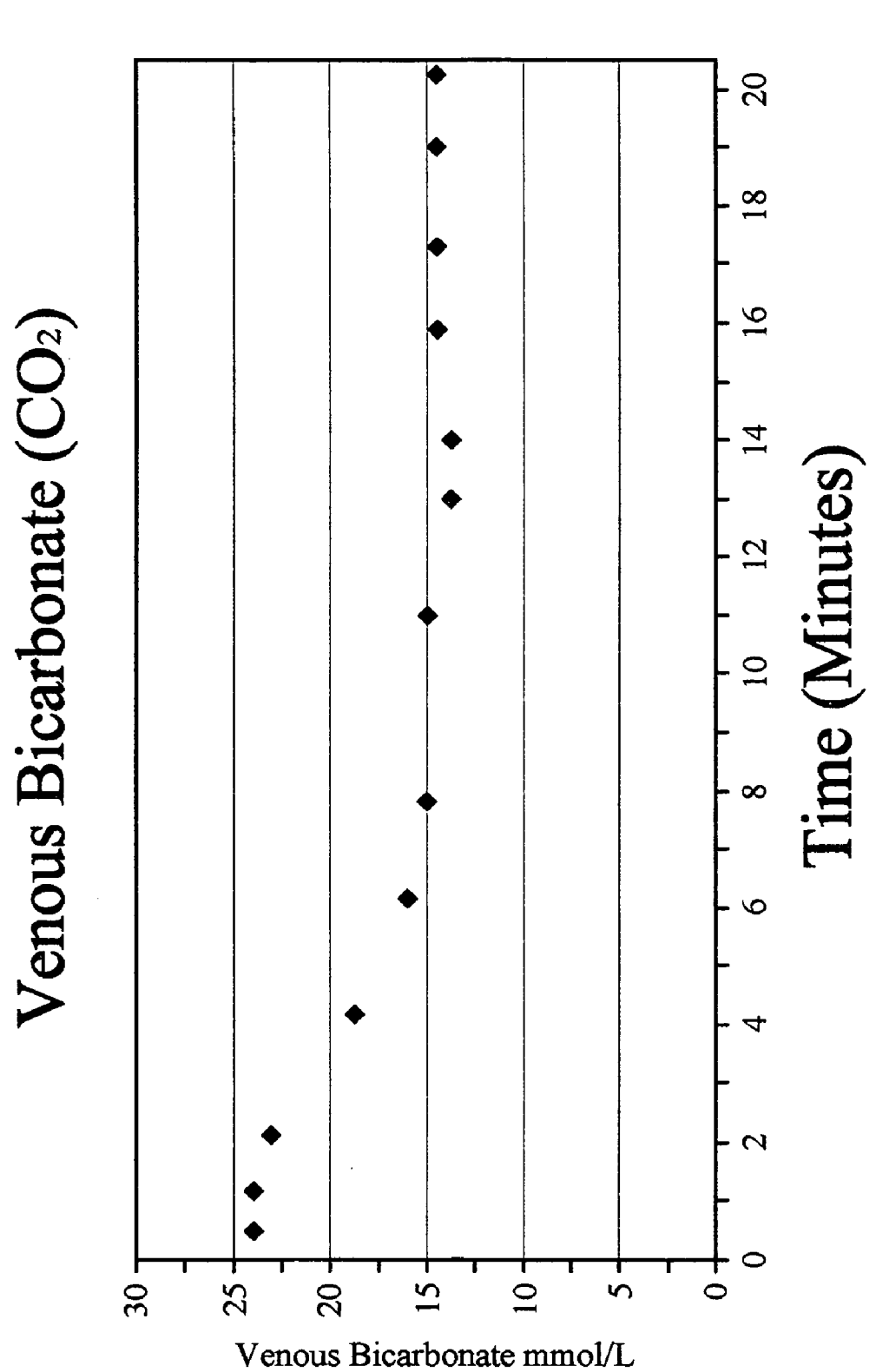
FIG. 16 shows venous bicarbonate ($CO_2$) as a function of time in an experimental subject in an embodiment of the instant invention.

$TCO_2$ (FIG. 15) and venous bicarbonate (FIG. 16) together trended in a similar pattern but for different reasons. As stated above, $TCO_2$ was immediately, intentionally and aggressively dropped to maximize the alkaline buffering reserve. The drop in bicarbonate occurred at a later time because it is also dependent on lactate levels. The bicarbonate trend was inverse to that of lactate levels. The athlete entered the testing near the low $TCO_2$ established by the Incremental Maximum Effort Test. Within one and a half minutes, $TCO_2$ had dropped to 26. The minimum $TCO_2$ value was 23. This value also represented a steady-state level for the maximum effort test. This represents a drop (from baseline of 40) of 42%. Bicarbonate levels dropped to a low of 13 mmol/L with final steady-state levels of approximately 13-14 mmol/L. This level represents a decline of 46-50%, using reference resting levels of 26 mmol/L.

Figure 17:
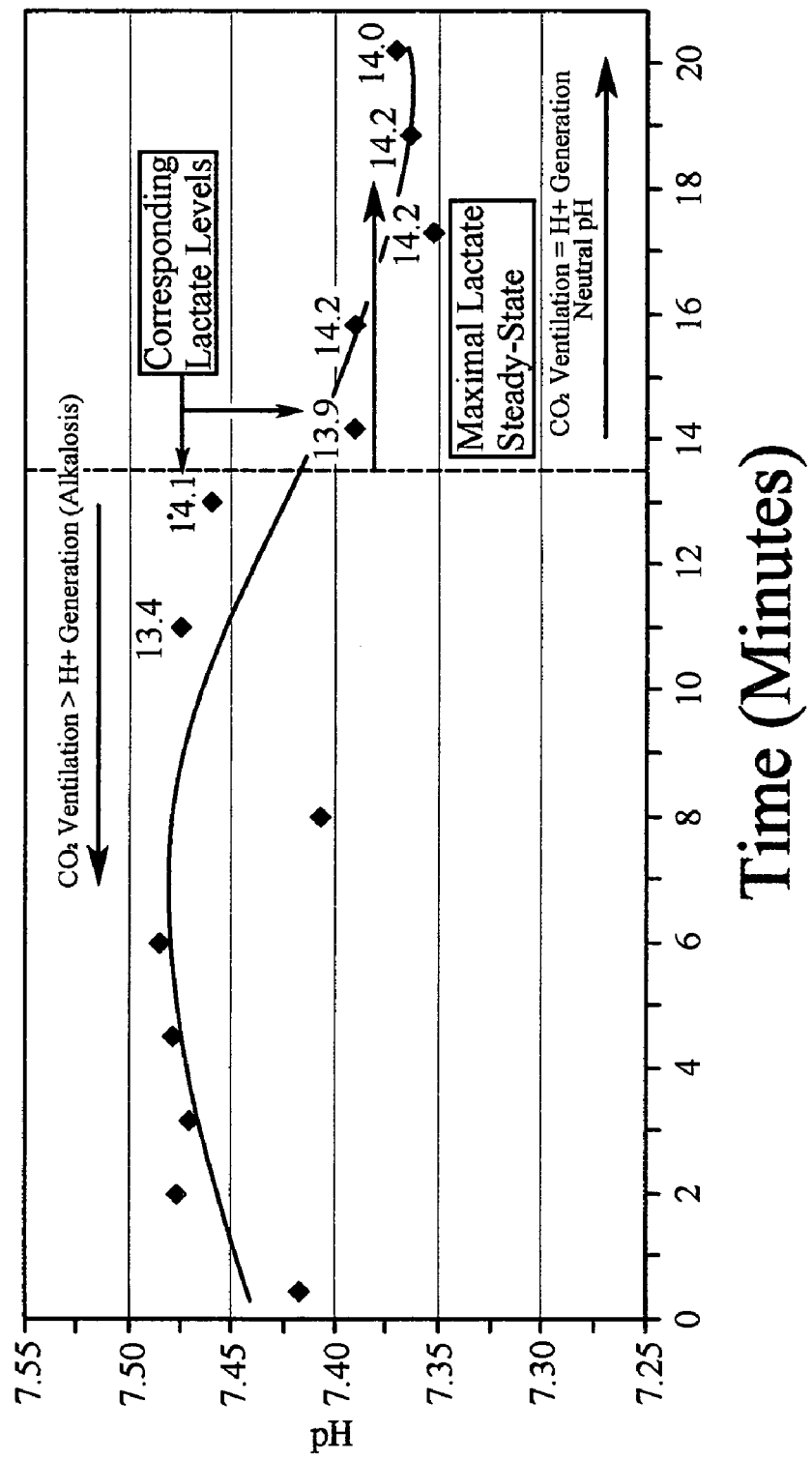
FIG. 17 shows venous pH as a function of time in an experimental subject in an embodiment of the instant invention, further showing a calculated trend line for the recorded values.

Venous pH, seen in FIG. 17, did not at any time enter the range of acidosis (pH less than 7.35), for the entire 20-minute duration of maximum effort. The pH quickly rose to an alkalotic range within the first one and a half minutes. There was a steep drop in pH after 14 minutes down to a neutral pH. For the initial 14 minutes, maximum effort was performed in an alkalotic pH environment as lactate slowly accumulated, and again, not exponentially, as would be predicted by the prior art. The final 6 minutes of maximum effort was performed in a neutral pH environment. This may reflect a failure of ventilatory endurance or mental alertness or even a change in the cellular physiology.

Venous pH, seen in FIG. 17, shows the end-result of the training methods of the instant invention and vividly illustrates that at supra-maximum efforts, an athlete, using the instant invention, can exercise without acidosis.

Figure 18:
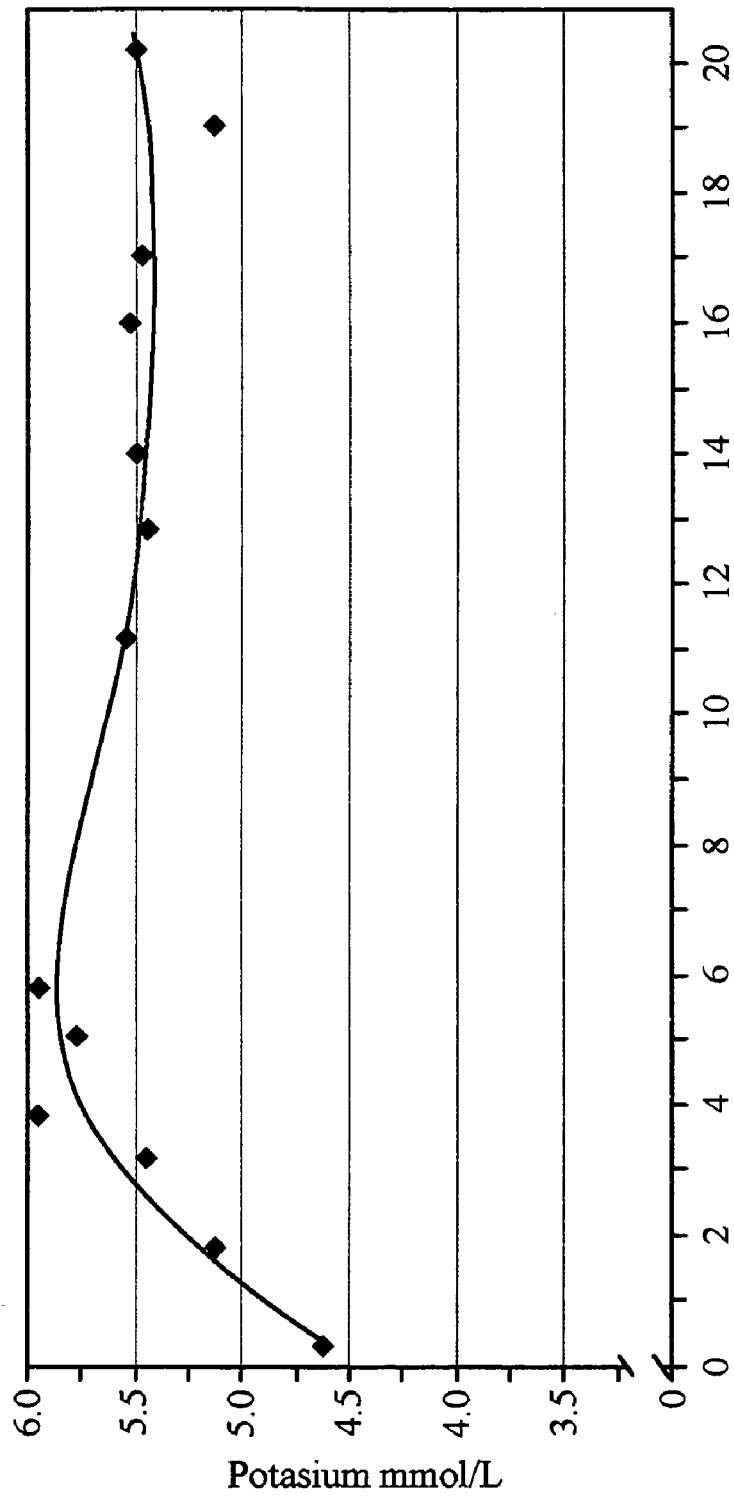
FIG. 18 shows potassium levels as a function of time in an experimental subject in an embodiment of the instant invention, further showing a calculated trend line for the recorded values

Alkaline pH's are maintained up until lactate levels reach approximately 14 mmol/L. At 14 mmol/L, pH drops to no less than a neutral pH. Small incremental increases in lactate at this level result in proportional decreases in $HCO_3^-$ but disproportionately large drops in pH. The MLSS is maintained in an alkalotic and at least neutral pH state. This illustrates how close to true maximum effort the athlete is, i.e., if lactate levels continue to rise, even in very small amounts, the athlete may develop a precipitous acidosis and exhaustion. As alkalosis is known to promote hypokalemia, and, in fact, an emergency treatment for hyperkalemia is injection of bicarbonate, there was concern that the alkalosis of the instant invention might adversely affect blood potassium levels. This however, is not the case, as seen in FIG. 18.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials and equipment, and relative arrangement of steps and elements. Accordingly, even though only few variations of the present invention are described herein, it is to be understood that the practice of such additional modifications and variations and the equivalents thereof, are within the spirit and scope of the invention as defined in the following claims. The corresponding structures, materials, acts, and equivalents of all means or step plus function elements in the claims below are intended to include any structure, material, or acts for performing the functions in combination with other claimed elements as specifically claimed.

I claim:

1. A method for enhanced transcutaneous carbon dioxide (TCO2) control exercise training of a trainee, comprising the steps of:

a) performing a first exercise training session during which the trainee is monitored with at least a cardiovascular characteristic monitor, a metabolic characteristic monitor, and a TCO2 monitor, further comprising the steps of;
   1) recording the TCO2 of the trainee at rest, thereby establishing a first baseline TCO2 value;
   2) initiating exercise of the trainee at progressively increasing intensity, while allowing the trainee to view the TCO2 monitor, both monitoring and recording, (i) at least one primary cardiovascular characteristic value reflecting exercise intensity, (ii) at least one primary metabolic characteristic value reflecting blood acid-base balance, and (iii) at least one TCO2 value; at least at a first and a second time;
   3) continuing to progressively increase the exercise intensity of the trainee, as measured by the primary cardiovascular characteristic value, to a point of maximum effort and both monitoring and recording a measured maximum effort cardiovascular characteristic value reflecting the primary cardiovascular characteristic value at the point of maximum effort;
   4) determining a maximum cardiovascular characteristic value reflecting exercise intensity selected from one of the group of values consisting of (i) an age determined formula based maximum heart rate value for the trainee and (ii) the recorded measured maximum effort cardiovascular characteristic value;
   5) correlating the at least one primary cardiovascular characteristic value with the at least one metabolic characteristic value for each of the at least first and second times;
   6) determining, by reference to a predetermined reference criteria, a lactate threshold (LT) value selected from a group of values consisting of the at least one primary metabolic characteristic value;
   7) determining the recorded primary cardiovascular characteristic value at the LT value;
   8) calculating a target cardiovascular characteristic value, less by a predetermined measure, than the recorded primary cardiovascular characteristic value at the LT value; and
   9) resting the trainee for a time sufficient to attain a training baseline TCO2 value not greater than 110% of the first baseline TCO2; and b) performing at least one secondary exercise training session during which the trainee is monitored with at least a cardiovascular characteristic monitor and a TCO2 monitor, further comprising the steps of;
   1) initiating exercise of the trainee at progressively increasing intensity, as measured by the primary cardiovascular characteristic value and monitoring and recording TCO2 values while allowing the trainee to view the TCO2 monitor, to a steady state exercise intensity at which the trainee attains the target cardiovascular characteristic value;
   2) identifying a sensed somatic state by instructing the trainee to increase ventilation to reduce the monitored and recorded TCO2 values to an at least one predetermined TCO2 value, while instructing the trainee to identify and correlate at least one physiologic sensation with the at least one predetermined TCO2 value;
   3) resting the trainee for a time sufficient to attain the training baseline TCO2 value; and c) repeating the secondary exercise training session until the trainee is able to identify the sensed somatic state without viewing the TCO2 monitor;

d) verifying that the identification of the sensed somatic state by the trainee correlates to within a first predetermined range above and below the at least one predetermined TCO2 value;
   1) resting the trainee for a time sufficient to attain the training baseline TCO2 value; and
e) performing at least one tertiary exercise training session during which the trainee is monitored with at least a cardiovascular characteristic monitor and a TCO2 monitor, further comprising the steps of;
   1) initiating exercise of the trainee at progressively increasing intensity, as measured by the primary cardiovascular characteristic value, while not allowing the trainee to view the TCO2 monitor;
   2) monitoring the primary cardiovascular characteristic value;
   3) continuing to progressively increase the exercise intensity of the trainee to a point at which the trainee attains the target cardiovascular characteristic value;
   4) instructing the trainee to adjust ventilation to achieve an at least one predetermined TCO2 value based on the perception of the sensed somatic state; and
   5) verifying that the trainee has adjusted ventilation so as to attain at least one of the predetermined TCO2 values within a second predetermined range above and below the at least one predetermined TCO2 value.

2. The method according to claim 1, wherein the cardiovascular characteristic monitor further includes at least a heart rate monitor.

3. The method according to claim 2, wherein the cardiovascular characteristic monitor further includes at least a pulse oximeter.

4. The method according to claim 1, wherein the metabolic characteristic monitor further comprises at least one laboratory measurement value derived from a laboratory measurement performed on a quantity of blood selected from the group of venous blood and capillary blood.

5. The method according to claim 4, wherein the at least one laboratory measurement value includes at least one laboratory measurement value selected from a group of consisting of measurement of venous or capillary lactate, venous or capillary CO2 (bicarbonate (HCO3-)), and venous or capillary pH values.

6. The method according to claim 5, wherein the at least one primary metabolic characteristic value reflecting acid base balance is an acid base balance value selected from the group of laboratory measurement values selected from the group consisting of venous or capillary lactate, venous or capillary CO2 (HCO3-), and venous or capillary pH values.

7. The method according to claim 1, wherein exercise at progressively increasing intensity further comprises at least a first level and a second level of exercise intensity performed at a predetermined exercise intensity for a predetermined period of time.

8. The method according to claim 1, wherein the at least one primary cardiovascular characteristic value reflecting exercise intensity is heart rate.

9. The method according to claim 1, wherein the age determined formula based maximum heart rate value is calculated by subtracting an age of the trainee in years from 220.

10. The method according to claim 1, wherein the predetermined measurement criteria determining the LT value is further determined as a first occurring in time venous lactate value having a value greater than 2.0 mmol/l during exercise of progressively increasing intensity.

11. The method according to claim 1, wherein the predetermined measurement criteria determining the LT value is further determined as a first occurring in time primary metabolic characteristic value selected from the group of values reflecting a rise in value of at least 50% over baseline values and a value of blood lactate greater than 2.0 mmol/l, and a laboratory lactate level greater than the standardized normal values for the assay, during exercise of progressively increasing intensity.

12. The method according to claim 1, wherein the calculation of the target cardiovascular characteristic value is equal to or more than 0.95 of the primary cardiovascular value at the LT value.

13. The method according to claim 1, wherein the calculation of the target cardiovascular characteristic value is equal to or more than 0.90 of the primary cardiovascular value at the LT Value.

14. The method according to claim 1, wherein the calculation of the target cardiovascular characteristic value is equal to or more than 0.80 of the primary cardiovascular value at the LT Value.

15. The method according to claim 1, wherein the at least one predetermined TCO2 value is equal to or more than 95% of the first baseline TCO2 value.

16. The method according to claim 1, wherein the at least one predetermined TCO2 value is equal to or more than 90% of the first baseline TCO2 value.

17. The method according to claim 1, wherein the at least one predetermined TCO2 value is equal to or more than 80% of the first baseline TCO2 value.

18. The method according to claim 1, wherein the at least one predetermined TCO2 value is equal to or more than 70% of the first baseline TCO2 value.

19. The method according to claim 1, wherein the first predetermined range above and below the at least one predetermined TCO2 value is a range of less than or equal to 2 mmHg above and below the at least one predetermined TCO2 value.

20. The method according to claim 1, wherein the first predetermined range above and below the at least one predetermined TCO2 value is a range of less than or equal to 5 mmHg above and below the at least one predetermined TCO2 value.

21. The method according to claim 1, wherein the second predetermined range above and below the at least one predetermined TCO2 value is a range of less than or equal to 2 mmHg above and below the at least one predetermined TCO2 value.

22. The method according to claim 1, wherein the second predetermined range above and below the at least one predetermined TCO2 value is a range of less than or equal to 5 mmHg above and below the at least one predetermined TCO2 value.

23. A method for enhanced transcutaneous carbon dioxide (TCO2) control exercise training of a trainee, comprising the steps of:
   a) performing a first exercise training session during which the trainee is monitored with at least a cardiovascular characteristic monitor, a metabolic characteristic monitor, and a TCO2 monitor, further comprising the steps of;
      1) recording the TCO2 of the trainee at rest, thereby establishing a first baseline TCO2 value;
      2) initiating exercise of the trainee at progressively increasing intensity, while allowing the trainee to view the TCO2 monitor, both monitoring and recording, (i) at least one primary cardiovascular characteristic value reflecting exercise intensity, (ii) at least one primary metabolic characteristic value reflecting blood acid-base balance, and (iii) at least one TCO2 value; at least at a first and a second time;

3) continuing to progressively increase the exercise intensity of the trainee, as measured by the primary cardiovascular characteristic value, to a point of maximum effort and both monitoring and recording a measured maximum effort cardiovascular characteristic value reflecting the primary cardiovascular characteristic value at the point of maximum effort;

4) determining a maximum cardiovascular characteristic value reflecting exercise intensity selected from one of the group of values consisting of (i) an age determined formula based maximum heart rate value for the trainee and (ii) the recorded measured maximum effort cardiovascular characteristic value;

5) correlating the at least one primary cardiovascular characteristic value with the at least one metabolic characteristic value for each of the at least first and second times;

6) determining, by reference to a first occurring in time venous lactate value having a value greater than 2.0 mmol/l during exercise of progressively increasing intensity, a lactate threshold (LT) value selected from a group of values consisting of the at least one primary metabolic characteristic value;

7) determining the recorded primary cardiovascular characteristic value at the LT value;

8) calculating a target cardiovascular characteristic value, less by a predetermined measure, than the recorded primary cardiovascular characteristic value at the LT value; and 9) resting the trainee for a time sufficient to attain a training baseline TCO2 value not greater than 110% of the first baseline TCO2; and b) performing at least one secondary exercise training session during which the trainee is monitored with at least a cardiovascular characteristic monitor and a TCO2 monitor, further comprising the steps of;

1) initiating exercise of the trainee at progressively increasing intensity, as measured by the primary cardiovascular characteristic value and monitoring and recording TCO2 values while allowing the trainee to view the TCO2 monitor, to a steady state exercise intensity at which the trainee attains the target cardiovascular characteristic value;

2) identifying a sensed somatic state by instructing the trainee to increase ventilation to reduce the monitored and recorded TCO2 values to an at least one predetermined TCO2 value, while instructing the trainee to identify and correlate at least one physiologic sensation with the at least one predetermined TCO2 value;

3) resting the trainee for a time sufficient to attain the training baseline TCO2 value; and c) repeating the secondary exercise training session until the trainee is able to identify the sensed somatic state without viewing the TCO2 monitor;

d) verifying that the identification of the sensed somatic state by the trainee correlates to within a first predetermined range above and below the at least one predetermined TCO2 value further comprising a range of less than or equal to 5 mmHg above and below the at least one predetermined TCO2 value;

1) resting the trainee for a time sufficient to attain the training baseline TCO2 value; and e) performing at least one tertiary exercise training session during which the trainee is monitored with at least a cardiovascular characteristic monitor and a TCO2 monitor, further comprising the steps of;

1) initiating exercise of the trainee at progressively increasing intensity, as measured by the primary cardiovascular characteristic value, while not allowing the trainee to view the TCO2 monitor;

2) monitoring the primary cardiovascular characteristic value;

3) continuing to progressively increase the exercise intensity of the trainee to a point at which the trainee attains the target cardiovascular characteristic value;

4) instructing the trainee to adjust ventilation to achieve an at least one predetermined TCO2 value based on the perception of the sensed somatic state; and 5) verifying that the trainee has adjusted ventilation so as to attain at least one of the predetermined TCO2 values within a second predetermined range above and below the at least one predetermined TCO2 value.

24. The method according to claim 23, wherein the second predetermined range above and below the at least one predetermined TCO2 value is a range of less than or equal to 5 mmHg above and below the at least one predetermined TCO2 value.

* * * * *